United States Patent
Mao et al.

(10) Patent No.: US 9,380,966 B2
(45) Date of Patent: Jul. 5, 2016

(54) TISSUE RETRACTOR OXIMETER

(75) Inventors: Jimmy Jian-min Mao, Fremont, CA (US); Robert E. Lash, Redwood, CA (US)

(73) Assignee: ViOptix, Inc., Fremont, CA (US)

( * ) Notice: Subject to any disclaimer, the term of this patent is extended or adjusted under 35 U.S.C. 154(b) by 2099 days.

(21) Appl. No.: 12/126,860

(22) Filed: May 24, 2008

(65) Prior Publication Data

US 2008/0319290 A1    Dec. 25, 2008

Related U.S. Application Data

(63) Continuation-in-part of application No. 29/281,422, filed on Jun. 22, 2007, now Pat. No. Des. 582,034, and a continuation-in-part of application No. 29/284,438, filed on Sep. 7, 2007, now Pat. No. Des. 574,493, and a continuation-in-part of application No. 29/284,745, filed on Sep. 14, 2007, now Pat. No. Des. 574,955, and a continuation-in-part of application No. 29/298,455, filed on Dec. 5, 2007, now Pat. No. Des. 578,647.

(51) Int. Cl.
  *A61B 5/145*    (2006.01)
  *A61B 5/1459*   (2006.01)
  *A61B 17/02*    (2006.01)
  *A61B 5/00*     (2006.01)

(52) U.S. Cl.
  CPC ......... *A61B 5/14542* (2013.01); *A61B 5/0086* (2013.01); *A61B 5/1459* (2013.01); *A61B 5/6846* (2013.01); *A61B 17/02* (2013.01); *A61B 5/0002* (2013.01); *A61B 2017/0262* (2013.01); *A61B 2562/225* (2013.01)

(58) Field of Classification Search
  CPC ............ A61B 17/02; A61B 17/0206; A61B 5/14551–5/14557; A61B 5/0261
  USPC ......... 600/322, 323, 324, 325, 326, 327, 328, 600/339, 340, 341, 342, 344
  See application file for complete search history.

(56) References Cited

U.S. PATENT DOCUMENTS

| | | | |
|---|---|---|---|
| 3,394,700 A | 7/1968 | Yamamoto | |
| 4,049,000 A | 9/1977 | Williams | |
| 4,190,042 A | 2/1980 | Sinnreich | |
| 4,226,228 A * | 10/1980 | Shin .................. | A61B 1/32 600/206 |
| D275,227 S | 8/1984 | Garner, Jr. | |
| 4,597,382 A | 7/1986 | Perez, Jr. | |
| 4,738,248 A | 4/1988 | Ray | |
| 4,784,150 A * | 11/1988 | Voorhies et al. ............. | 600/473 |
| 4,919,616 A | 4/1990 | Croll | |
| 4,945,896 A * | 8/1990 | Gade .................. | A61B 5/0084 600/202 |

(Continued)

FOREIGN PATENT DOCUMENTS

WO    2007099576 A2    9/2007

OTHER PUBLICATIONS

Nerve Root Retractors, Codman Surgical Product Catalog 380-385 (2004).

(Continued)

*Primary Examiner* — Adam J Eiseman
(74) *Attorney, Agent, or Firm* — Aka Chan LLP

(57) ABSTRACT

A retractor has an oximeter sensor at its tip, which allows measuring of oxygen saturation of a tissue being retracted by the retractor. The tip includes one or more openings for at least one source and detector. A specific implementation is a spinal nerve root retractor with an oximeter sensor.

37 Claims, 19 Drawing Sheets

(56) References Cited

U.S. PATENT DOCUMENTS

| | | | |
|---|---|---|---|
| 4,959,067 | A | 9/1990 | Muller |
| D312,306 | S | 11/1990 | Michelson |
| D318,116 | S | 7/1991 | Michelson |
| 5,123,403 | A | 6/1992 | Lavyne |
| 5,520,611 | A | 5/1996 | Rao et al. |
| 5,529,571 | A * | 6/1996 | Daniel ............... 600/219 |
| 5,769,781 | A | 6/1998 | Chappuis |
| 5,803,904 | A | 9/1998 | Mehdizadeh |
| 5,891,018 | A | 4/1999 | Wells |
| D411,883 | S | 7/1999 | Farascioni et al. |
| D420,130 | S | 2/2000 | Nicholas et al. |
| 6,078,833 | A | 6/2000 | Hueber |
| D430,668 | S | 9/2000 | Koros et al. |
| D433,134 | S | 10/2000 | Pitesky |
| D442,687 | S | 5/2001 | Schulz |
| D443,056 | S | 5/2001 | Koros et al. |
| D453,377 | S | 2/2002 | Schollhorn et al. |
| D457,957 | S | 5/2002 | Sanford et al. |
| 6,416,465 | B2 * | 7/2002 | Brau ............... A61B 17/02 600/210 |
| 6,516,209 | B2 | 2/2003 | Cheng et al. |
| 6,587,701 | B1 | 7/2003 | Stranc et al. |
| 6,735,458 | B2 | 5/2004 | Cheng et al. |
| 6,875,173 | B2 | 4/2005 | Suddaby |
| D510,768 | S | 10/2005 | Farley |
| 6,994,548 | B2 * | 2/2006 | Perret, Jr. ............... A61C 3/00 433/141 |
| D533,946 | S | 12/2006 | Lintner et al. |
| 7,206,621 | B2 * | 4/2007 | Aoyagi et al. ............... 600/323 |
| 7,226,413 | B2 * | 6/2007 | McKinley ............ A61B 17/025 600/210 |
| 2004/0039270 | A1 | 2/2004 | Keller et al. |
| 2007/0215824 | A1 | 9/2007 | Takeda et al. |
| 2008/0045822 | A1 * | 2/2008 | Phillips et al. ............... 600/323 |
| 2009/0259106 | A1 * | 10/2009 | Catapano et al. ............. 600/202 |

OTHER PUBLICATIONS

D.M. Hueber et al., "New Optical Probe Designs for Absolute (Self Calibrating) NIR Tissue Hemoglobin Measurements", Proc. SPIE 3597, pp. 618-631, Jan. 1999.

H. Taitelbaum et al., "Approximate theory of photon migration in a two-layer medium", Applied Optics, vol. 28, No. 12, pp. 2245-2249, Jun. 15, 1989.

S.J. Matcher et al., "Absolute qualification methods in tissue near infrared spectroscopy", Proc. SPIE vol. 2389, pp. 486-495, 1995.

D.T. Deply et al., "Quantification in tissue near-infrared spectroscopy", Phil. Trans. R. Soc. Lond. B352, pp. 649-659, 1997.

* cited by examiner

TISSUE RETRACTOR OXIMETER

CROSS-REFERENCE TO RELATED APPLICATIONS

This patent application is a continuation-in-part of U.S. design patent applications 29/298,455, filed Dec. 5, 2007; 29/284,745, filed Sep. 14, 2007; 29/284,438, filed Sep. 7, 2007; and 29/281,422, filed Jun. 22, 2007, which are incorporated by reference along with all other references cited in this application.

BACKGROUND OF THE INVENTION

This invention relates to the field of medical devices and more specifically to a tissue retractor with an oximeter sensor.

Retractors play an important role in medicine. Retractors typically retract or hold aside tissues (e.g., nerve) so that a physician (e.g., surgeon) can gain access to an area for operation or observation. It is critical that the retracted tissue is not damaged.

One function of a retractor is to retract a nerve, such as a spinal nerve root during spinal surgery. Tens of thousands of spinal surgeries are performed each year. The number of spinal surgeries is continuing to increase due, in part, to an aging population, active lifestyles, and a better understanding of what causes back pain. Back pain may be due to disc herniation, degenerative disc disease, spinal trauma, and osteoarthritis just to name a few examples.

The spinal cord is the main pathway through which the brain sends and receives signals. The nerve fibers in the spinal cord branch off to form pairs of nerve roots that travel through small openings between the vertebrae. These nerves control the body's function including the vital organs, sensation, and movement.

During spinal surgery, it is often necessary to retract the nerve root so that the surgeon can access the surgical site. With current medical devices, however, it is difficult if not impossible, to tell whether the nerve root is being damaged during the retraction. Damage to the nerve root or any nerve can be catastrophic.

There is, then, a continuing demand for medical devices that provide patient feedback, provide more features, are easier to use, and generally address the needs of patients, doctors, and others in the medical community.

Therefore, there is a need to provide improved systems and techniques for retractors.

BRIEF SUMMARY OF THE INVENTION

A retractor has an oximeter sensor at its tip, which allows measuring of oxygen saturation of a tissue being retracted by the retractor. The tip includes one or more openings for at least one source and detector. A specific implementation is a spinal nerve root retractor with an oximeter sensor.

In an embodiment, the invention is a device that includes a shaft, a handle, connected to a proximal end of the shaft, a tip, connected to a distal end of the shaft, comprising a retractor portion and an oximeter sensor. The device further includes a first optical fiber and a second optical fiber. The first optical fiber passes through a channel in the shaft and a distal end of the first optical fiber is coupled to a first sensor opening of the tip. The second optical fiber passes through the channel in the shaft and a distal end of the second optical fiber is coupled to a second sensor opening of the tip.

The device further includes a system unit including a display, processor, signal emitter circuit, signal detector circuit, and a receptacle to couple to proximal ends of the first and second optical fibers. The signal emitter circuit sends a signal through the optical fiber and the signal detector circuit receives the signal from the second optical fiber. The receptacle may be removably coupled to proximal ends of the first and second optical fibers.

The system unit may include a power management circuit and a battery. When the power management circuit detects a low battery condition, the power management circuit causes a warning to show on the display.

In an embodiment, the oximeter sensor includes the first sensor opening and second sensor opening on a bottom side of the tip. The first sensor opening and second sensor opening may be separated by about five millimeters or less.

The signal emitter circuit may include at least one of a laser emitter or light emitting diode (LED) emitter. The signal emitter circuit may further cause an optical signal, having a wavelength from about 600 nanometers to about 900 nanometers, to be transmitted through the first sensor opening. Furthermore, the signal emitter circuit may cause an optical signal having a two or more different wavelengths to be transmitted through the first sensor opening.

A first wavelength of the two or more different wavelengths may be about 690 nanometers. A second wavelength of the two or more different wavelengths may be about 830 nanometers.

In an embodiment to measure oxygen saturation of tissue touching the tip of device, the system unit determines a first quantity corresponding to an intensity of light of a first wavelength transmitted from the first sensor opening of the tip through the tissue to the second sensor opening of the tip, determines a second quantity corresponding to an intensity of light of a second wavelength transmitted from the first sensor opening of the tip through the tissue to the second sensor opening of the tip, where the second wavelength is different from the first wavelength, and calculates an attenuation ratio of the first quantity to the second quantity.

In an embodiment, the oximeter sensor includes three or more holes in a linear arrangement on a bottom side of the tip. In a further embodiment where the oximeter sensor comprises three or more holes, any two of the three or more or more holes may be positioned in a linear arrangement on a bottom side of the tip.

The oximeter sensor may include a first sensor emitter opening, a second sensor emitter opening, a first sensor detector opening, and a second sensor detector opening. Any three of the openings may be positioned in a linear arrangement on a bottom side of the tip.

In a specific embodiment, the second sensor emitter opening is between the first sensor emitter opening and the first sensor detector opening, and the first sensor detector opening is between the second sensor emitter opening and the second sensor detector opening.

The first sensor detector opening may be spaced away from the second sensor detector by about 5/3 millimeters or less, and the first sensor detector opening may be spaced away from the second sensor emitter opening by about 5/3 millimeters or less.

In an embodiment, the invention is a device including a shaft, a handle, connected to a proximal end of the shaft, a tip, connected to a distal end of the shaft, including an oximeter sensor having an opening with at least two light channels.

The opening may further include a first optical fiber and a second optical fiber. The opening may include a concentric core fiber, a split channel fiber, or both. The tip may further include a retractor blade.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
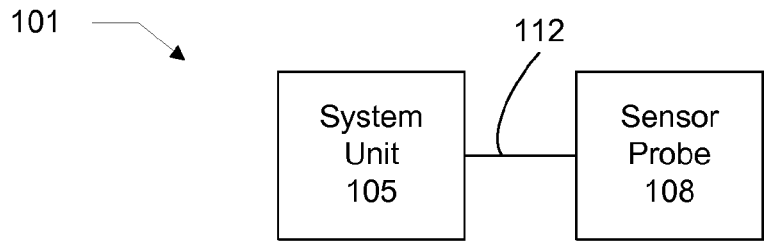
FIG. 1 shows an oximeter system for measuring oxygen saturation of tissue in a patient.

FIG. 1 shows an oximeter system 101 for measuring oxygen saturation of tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers). In other implementations of the invention, however, connection 112 may be wireless such as via a radio frequency (RF) or infrared communication.

Typically, the system is used by placing the sensor probe in contact or close proximity to tissue (e.g., skin or nerve) at a site where an oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no blood flow or pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbances of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
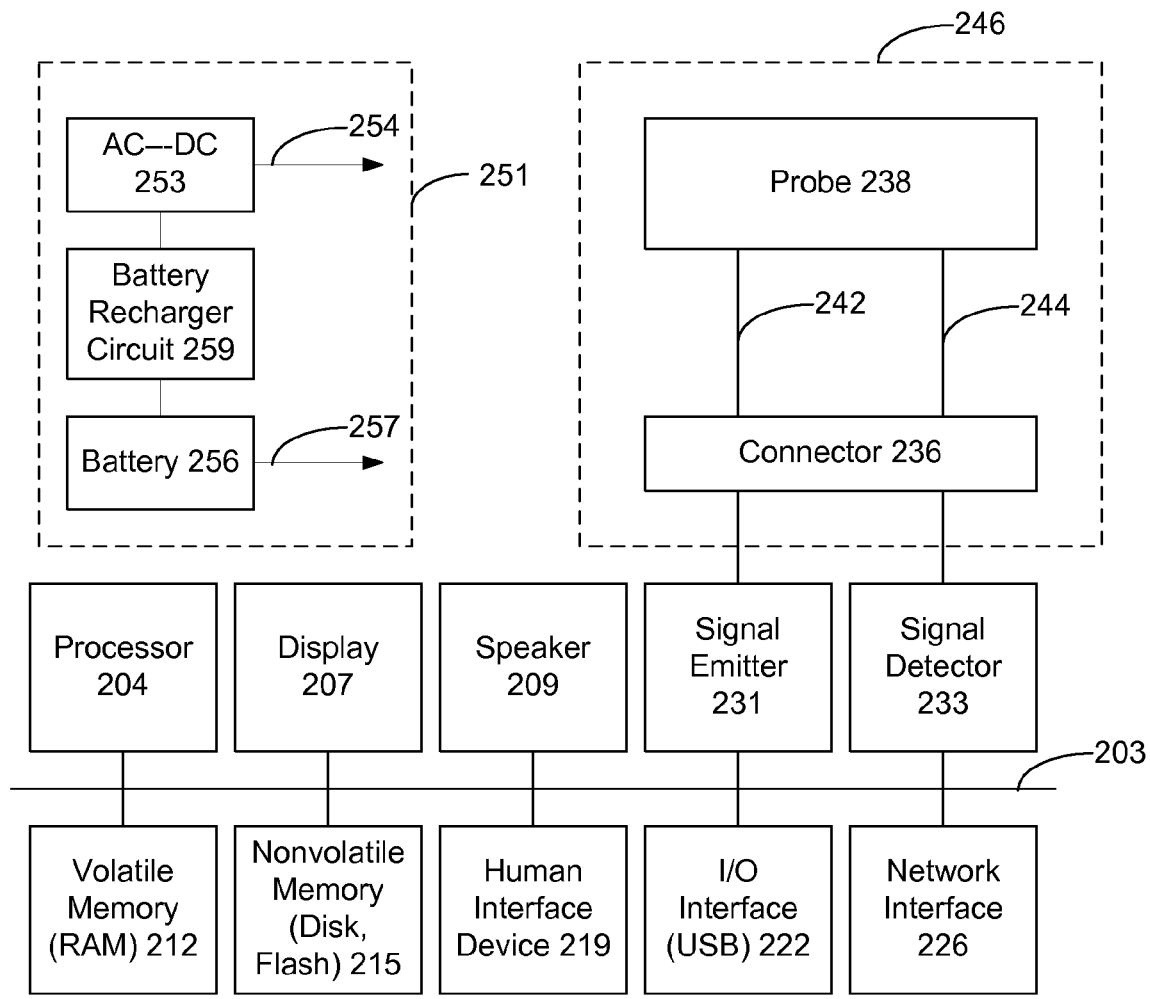
FIG. 2 shows detail of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. The second keying feature will let the system unit know which type of probe is connected, so that it can perform the right functionality, use the proper algorithms, or otherwise make adjustments in its the operation for a specific probe type.

In various implementations, the system is powered using a wall outlet or battery powered, or both. Block 251 shows power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
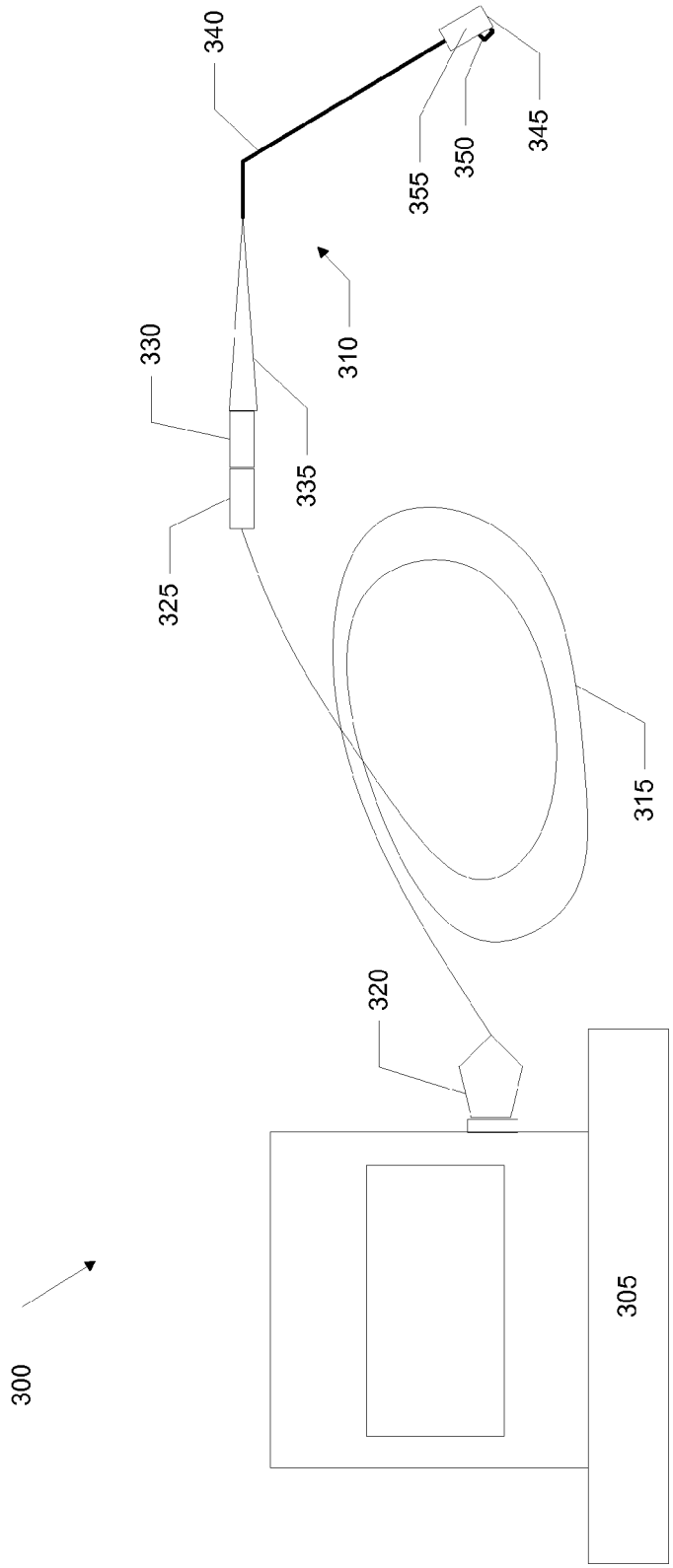
FIG. 3 shows a system of the invention including a monitoring console, a tissue retractor oximeter, and a cable connecting the retractor to the monitoring console.

FIG. 3 shows a system 300 of the invention including a monitoring console 305, a tissue retractor oximeter 310, and a cable 315 connecting the tissue retractor oximeter to the monitoring console. A connector 320 at a proximal end of the cable connects to the monitoring console while a connector 325 at a distal end of the cable connects to a connector 330 on the tissue retractor oximeter.

The tissue retractor oximeter, in addition to connector 330, includes a handle 335, a shaft 340 connected to the handle, and a tip 345 connected to an end of the shaft. The tip includes a retractor portion 350 and a sensor unit 355. In a specific embodiment, the sensor unit is omitted and the tip instead includes one or more optical fibers in an encasement.

The length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, or 2.5 meters long or greater. Depending on the specific application, the cable length may be less than 1.2 meters. In some applications, the cable length will be greater than 3 meters.

A specific application of the invention is operating room use or other places where it is desirable to maintain cleanliness and sterile conditions, such as isolation units. Patients in isolation units may have contagious diseases or compromised immune systems. Hospitals need to ensure that patients with a contagious disease do not infect others. Items introduced near the patient must either be disposed after use or properly cleaned. Hospitals also need to protect patients with compromised immune systems from sources of microorganisms. In these cases, a longer cable length, such as greater than 1.2 meters, is advantageous because this helps to separate the patient from sources of contamination, such as the console. Similarly, a longer cable length also minimizes contamination, such as contamination of the console, by the patient.

In a specific implementation, the tissue retractor oximeter, entire length of cable, and connectors are packaged as a probe unit in a sterile package. The probe unit is detachable from the console after use and may be disposed. A user may then open a new sterile package containing a new probe unit. The package may be opened at the time of actual use or near the time of actual use so as to not contaminate the probe unit. The user can then connect this new and sterile probe unit to the console to begin monitoring. This disposable feature provides an additional level of protection in maintaining a sterile field around the patient.

In another implementation, the sensor unit, entire length of cable, connectors, or combinations of these are detachable from the tissue retractor oximeter. The sensor unit, entire length of cable, connectors, or combinations of these may be packaged as a probe unit in a sterile package. After use, such as after spinal surgery, the user may detach the sensor unit and cable from the tissue retractor oximeter for disposal. The user may then open a new sterile package containing a new probe unit. The user can then attach the new sensor unit, cable, or both to the tissue retractor oximeter for future use.

Short cables pose a problem. Short cables bring whatever element they are connected to within close proximity to the patient. Doctors and nurses must then devote additional care and time to ensure a sterile field around the patient. This may include, for example, additional cleansing of the elements before and after introduction to the sterile field, or sterile drapes on the elements.

In a specific embodiment, there may be other connectors on the cable besides connectors 320 and 325. These other connectors allow the cable to be separated into two or more pieces, allow additional lengths of cable to be attached, or both.

These additional connectors provide several benefits. For example, the cable attached to the tissue retractor oximeter can be disposed along with the tissue retractor oximeter after use. The cables attached to the console can be reused. Thus, the cable more likely to be contaminated, i.e., the cable attached to the tissue retractor oximeter, can be disposed. The cable less likely to be contaminated, i.e., the cable attached to the console can be reused. As another example, the connectors may be used to attach additional lengths of cable to extend the overall length of the cable.

In an implementation, the cable includes one or more optical wave guides enclosed in a flexible cable jacket. The optical wave guides may be used to transmit light from the console, through the tissue retractor oximeter and out openings in the tip and into the tissue. The optical wave guides may also be used to transmit the light received from the tissue back to the console.

The optical wave guides may have the shape of a polygon, such as a square, rectangle, triangle, or other shape. In other cases, the optical wave guides may have circular or oval shapes. In a specific implementation, the optical wave guides are multiple strands of fiber optic cable. The flexible cable jacket may be thin-walled PVC with or without an aluminum helical monocoil, shrink wrap tubing, plastic, rubber, or vinyl.

In a specific embodiment, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In a specific implementation, the cable is passive. For example, it will not contain any active, generative properties to maintain signal integrity. However, in other implementations, the cable may include active components. The cable may include active components to amplify the signal transmitted through the sensor unit, received at the sensor unit, or both. For example, long lengths of cable subject to significant attenuation may require amplification. Amplification may also be required if the monitored site contains a particularly dense structure such as bone. In a specific implementation, radiation sources such as light emitting diodes (LEDs) may be placed in the sensor unit. Thus, the cable may contain electrical wiring to transmit power to the radiation sources.

In an embodiment of the invention, each opening on the sensor unit and corresponding cable is dedicated to a particular purpose. For example, a first opening on the sensor unit (and corresponding fiber optic cable) is dedicated to transmitting light from the monitoring console. A second opening on the sensor unit is dedicated to transmitting a signal received at the second opening to the monitoring console.

Some embodiments use a particular opening and cable for multiple purposes (e.g., both input and output) using a scheme such as multiplexing.

In a specific embodiment, a particular opening and cable transmits an output to affect a reaction (e.g., sending electrical signals to stimulate muscle or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's skin back to the monitoring device.

In an implementation, the connectors on the cable, monitoring console, tissue retractor oximeter, and combinations of these have indicators. The indicators may be color indicators that are painted on, or raised indicators, or both. These indicators help the user to properly attach the cable to the monitoring console, tissue retractor oximeter, or both. For example, the indicators may include green arrows placed on the cable connectors, monitoring console, and tissue retractor oximeter. Alignment of the arrows indicates proper attachment of the cables. Further, there may be instructions printed on the console, cable, and tissue retractor oximeter that instruct the user on the proper attachment of the cable.

The connectors at the ends of the cable attach to the monitoring console and tissue retractor oximeter. The connectors protect the cable from accidental disconnection. The connector may be a threaded collar on a cable end that threads onto the monitoring console or tissue retractor oximeter. Alternatively, the connector may be a lug closure, press-fit, or snap-fit.

In an implementation, the console is portable. Thus, the console can be hand-carried or mounted to an intravenous (IV) pole. A portable console can follow a patient anywhere in the hospital, eliminating the need to change connections whenever a patient is moved. Moreover, a portable design facilitates use and assessments in numerous other locations besides a hospital.

A portable console is typically battery-operated. The battery is typically a rechargeable type, such as having nickel cadmium (NiCd), nickel metal hydride (NiMH), lithium ion (Li-Ion), lithium polymer, lead acid, or another rechargeable battery chemistry. The system can operate for a certain amount of time on a single battery charge. After the battery is drained, it may be recharged and then used again.

The portable console may also have a power-saving feature. This reduces battery consumption during continuous measurements. The power-saving feature may, for example, darken the console's display screen after a certain time of inactivity. The time may be approximately five, ten, fifteen, or twenty minutes. Alternatively, the user may program the time.

The console may include a power management circuit. When the power management circuit detects a low battery condition, the power management circuit may cause a warning to show on the display. The power management circuit may include other features as well. For example, when the power management circuit detects a low battery condition (e.g., voltage drops below a threshold value), the power management circuit may cause the system to power down after a specified amount of time. The specified amount of time may be programmed by the user. As another example, when the power management circuit detects a low battery condition, and the system is in an off mode and AC input is not connected to the power source, the power management circuit will not permit the system to be powered to an on mode.

In a specific implementation, the portable console weighs approximately 4.3 kilograms. However, the weight may vary from about 3 kilograms to about 7 kilograms including, for example, 3.5, 4, 4.5, 5, 5.5, 6, 6.5, 7, or more than 7 kilograms.

In another implementation, the console is not hand-held or portable. The console may be a large, nonportable device that is attached to a wall or secured to a stand or surface. In this implementation, the system is typically connected to AC power. A battery may be used as a back-up to the AC power.

In a specific implementation, the console provides alerts. The alerts may be visual (e.g., a flashing light on a display of the console), audible, or both. Visual alerts may be designed so that they are viewable from any location (e.g., a flashing light on the top of the console). In a chaotic and noisy situation, this allows users to quickly respond to a patient. These alerts may signal a problem with the system. This includes, for example, insufficient signal strength, kinks or sharp bends in the cable, debris on the sensor unit, debris on a coupling surface between the cable and the console, insufficient electrical power, a low battery, an improperly attached cable, or other problem.

An alert may also signal when the system is ready for patient monitoring. The alerts may also provide warnings at certain oxygen saturation levels. For example, if the oxygen saturation level or other critical measurement falls below a threshold value then the system will provide an alert. In a specific embodiment, the alert is provided by the console. However, the alert may also be provided by the retractor. For example, the retractor may include warning lights. Such warning lights may be placed on the handle, shaft, or both. This allows the user to see, for example, whether the oxygen saturation level of the tissue being retracted has fallen below a threshold level, without having to turn and look at the console. Different alerts may be used depending on the type of problem detected by the system. Different alerts include different colors, sounds, and intensities of colors and sounds.

The console may provide an alert when the sensor unit is placed in a suitable location for a measurement. The alert may vary in intensity depending on the suitability of the location. The alert may be audible, or visual, or both. An audible alert allows the user to determine the suitability of a location without having to look away from the patient.

The alerts may be user-programmable. That is, users may set which alerts are enabled, the threshold at which they are activated, and the intensities of the alerts. For example, a user may decide to enable the oxygen saturation alert, set the alert to occur if and when the oxygen saturation level falls below a certain value, and set the volume level of the alert.

The console may also include a mass storage device to store data. Mass storage devices may include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

A screen on the console displays the patient's data, such as an oxygen saturation measurement. The screen may be a flat panel display such as a liquid crystal display (LCD), plasma display, thin film transistor liquid crystal display (TFT LCD), electro-luminescent (EL), or organic light emitting diode (OLED) display. The screen may include a touch screen interface. Such touch screen interfaces are easier to clean compared to keypads if they become contaminated because they do not contain mechanical parts.

The screen may display numbers, text, graphics, and graphical trends in color. Different colors may correspond to different measurements or threshold levels. The text and numbers may be displayed in specific languages such as English, Spanish, French, Japanese, or Tagalog. The displayed language is user-programmable.

In a specific implementation, the screen displays data related to a single regional oxygen saturation reading. For example, this may include a single plot or graph.

Users can also vary the size of the displayed information on the console's screen. This allows the display to be viewed at a distance, increases the viewing angle, and allows users with vision limitations to see the information.

The console, in addition to the display, may also include a processor, signal emitter circuit, signal detector circuit, and a receptacle to removeably couple ends of one or more optical fibers. In a specific implementation, the ends of one or more optical fibers are instead permanently connected to the console. The signal emitter circuit may operate to send a signal through the one or more optical fibers. The signal detector circuit then receives a signal via one or more optical fibers.

In a specific implementation, the console includes a first radiation source and a second radiation source. The radiation sources may be dual wavelength light sources. In other words, first radiation source provides two wavelengths of radiation and second radiation source provides two wavelengths of radiation. First radiation source, second radiation source, or both may include one or more laser diodes or light emitting diodes (LEDs) that produce light in any wavelength, but typically the wavelengths range from about 600 nanometers to about 900 nanometers. In a specific implementation a first wavelength of light is generated that has a wavelength of about 690 nanometers. A second wavelength of light is generated that has a wavelength of about 830 nanometers.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In a specific implementation, one or more near-infrared radiation sources are included within the console. In other implementations, the radiation sources may be external to the console. For example, the radiation sources may be contained within a separate unit between the console and sensor unit. The radiation sources may, for example, be contained in the handle of the tissue retractor oximeter. In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, 10 or more than 10 radiation sources. These radiation sources may generate approximately 30 milliwatts of power. However, the power can range from about 20 milliwatts to about 100 milliwatts of power or more. Depending on the application, the power may be less than 20 milliwatts.

Also, only a percentage of the power output of the source is transmitted to the tissue. For example, when the laser diode output is 30 milliwatts, the power that gets to the tissue will be about 3 milliwatts. So, approximately $1/10$ of the power of the laser diode is transmitted into the tissue.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

Figure 4:
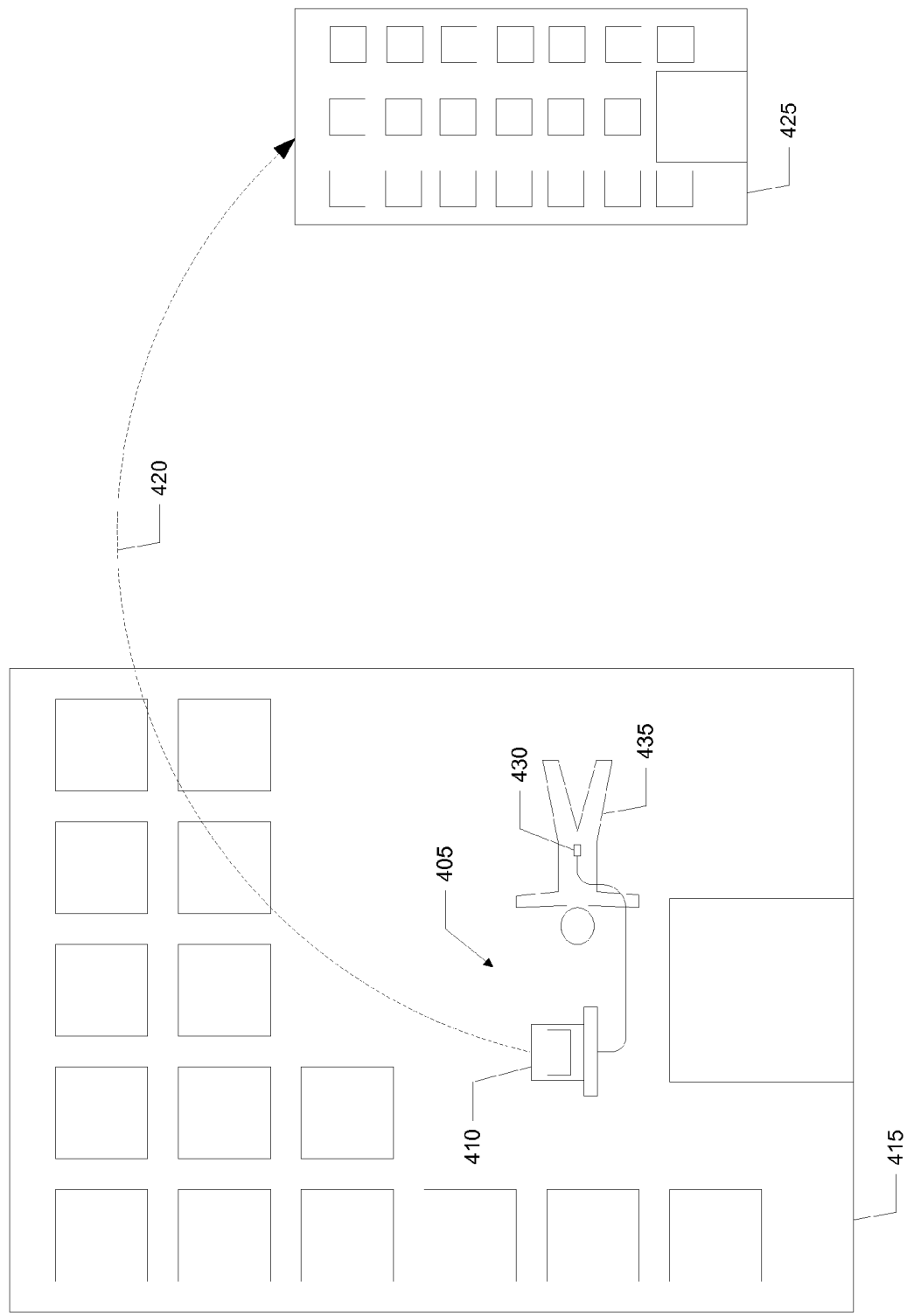
FIG. 4 shows an example of a wireless implementation of the invention.

FIG. 4 shows an example of a wireless implementation of the invention. A system 405 includes a monitoring console 410 at a field location 415 which transmits 420 the patient's data to a receiving location 425. The figure shows the monitoring console transmitting the data, using for example, a modem in the monitoring console. However, in another implementation, a tissue retractor oximeter 430 may wirelessly transmit the data the receiving location.

In the figure, the field location is in an operating room and a patient 435 is undergoing spinal surgery, such as spinal disk surgery. In other implementations, the field location may be a trailer, a tent, or in a vehicle such as a car, ambulance, automobile, truck, bus, train, plane, boat, ship, submarine, or helicopter. The field location may also be on a battlefield.

The receiving location also varies. The receiving location may be a hospital, clinic, trauma center, physician's home or office, or a nurse's home or office. The monitoring console or sensor unit may also transmit to multiple receiving locations. For example, data may be transmitted to both the hospital and the physician's home.

A variety of devices may receive the data. This includes, for example, a monitoring console, other monitoring stations, mobile devices (e.g., phones, pagers, personal digital assistants (PDAs), and laptops), or computers, or combinations of these.

The distance between the field and receiving location may vary. The field and receiving location could be in different countries, states, cities, area codes, counties, or zip codes. In other cases, the field location and receiving location may be in different parts of the same room or in different rooms in the same building.

The wireless transmission may be analog or digital. Although FIG. 4 shows the system transmitting data directly to the receiving location, this is not always the case. The system may relay data to the receiving location using intermediaries. For example, satellites may rebroadcast a transmission. While in one embodiment, a communication network is the Internet, in other embodiments, the communication network may be any suitable communication network including a local area network (LAN), a wide area network (WAN), a wireless network, an intranet, a private network, a dedicated network, phone lines, cellular networks, a public network, a switched network, and combinations of these and the like. Wireless technologies that the system may employ include: Wi-Fi, 802.11a, 802.11b, 802.11g, 802.11n, or Bluetooth, or combinations of these and the like. The system also has the ability to switch from one communication technique to another if, for example, the current network is unreliable or there is interference. The switch may either be automatic or manual.

The system's ability to wirelessly transmit data offers several advantages. For example, data received by the monitoring console may be wirelessly transmitted to the receiving location where the patient's medical records may be stored. The data may then be saved as part of the patient's medical history.

Figure 5:
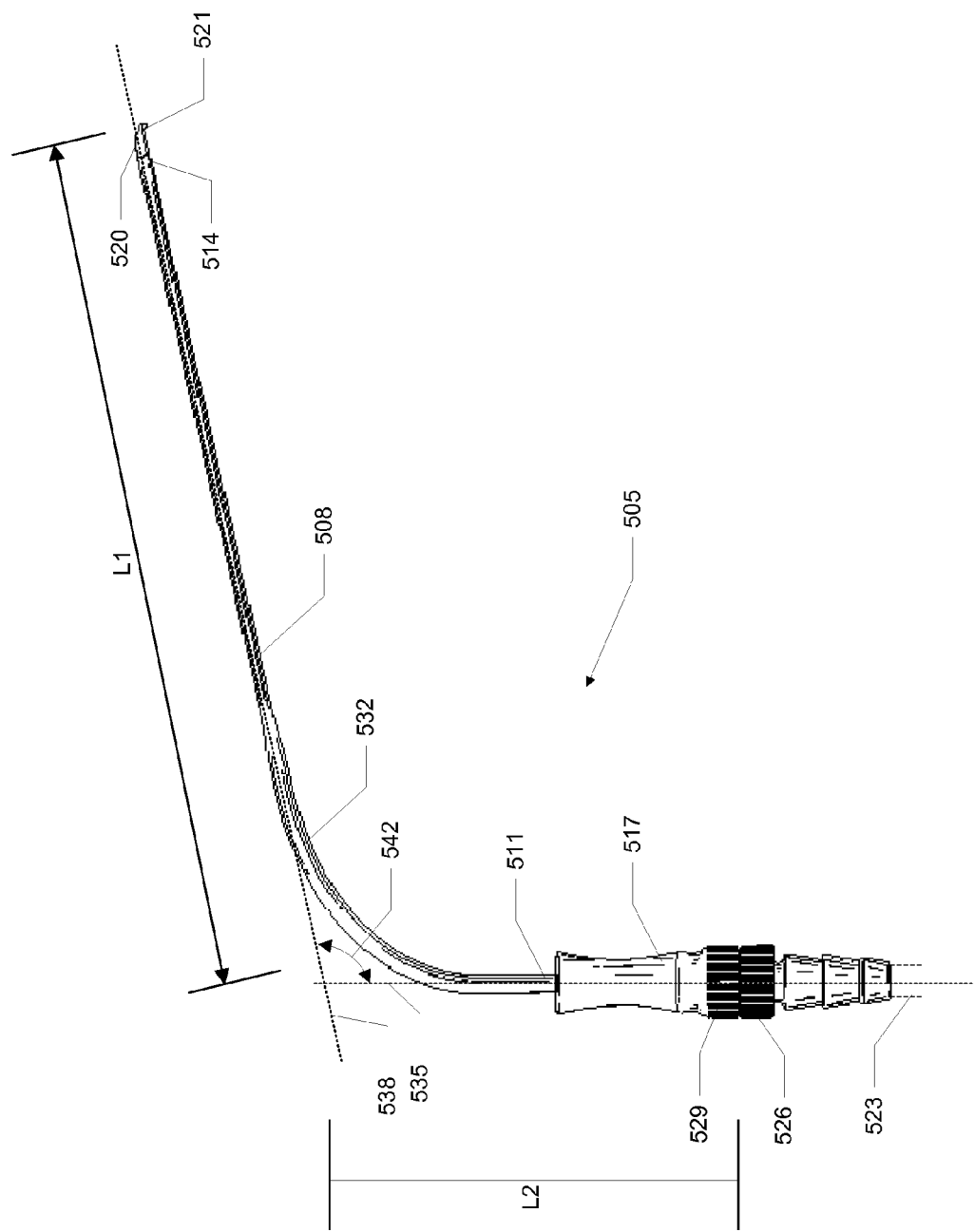
FIG. 5 shows a side view of a tissue retractor oximeter.

FIG. 5 shows a side view of a tissue retractor oximeter 505. The tissue retractor oximeter includes a shaft 508 with a proximal end 511 and a distal end 514. The proximal end of the shaft is connected to a handle 517. A tip 520 has a retractor portion or blade 521 and is connected to the distal end of the shaft. The figure also shows a cable 523 with a connector 526 that is connected to a connector 529 on the handle.

Although some specific dimensions, angles, and geometries, and retractor blades are shown and described in this application, one of skill in the art would understand that a retractor blade may be dimensioned or angled differently, so as to provide the appropriate control for a user (e.g., a surgeon) of the retractor and also as appropriate for the specific nerve or tissue being operated on. Further, the retractor may be adjustable such as having a variable length blade or a pivotable angle blade. And, the retractor portion or blade may have different shapes, such as a hook.

In a specific implementation, the shaft is hollow, including an internal channel or passageway 532 that runs the full length or some portion of the length of the shaft. The passageway may extend into the handle. The passageway is used to contain optical wave guides, electrical wiring, or other wiring, or combinations of these. In a specific embodiment, the shaft extends through the full length of the handle. In another embodiment, the shaft extends only through a portion of the handle. The shaft may be secured to the handle using an adhesive, a threaded connection, a lug closure (e.g., twist and lock), a press fit, or combinations of these. In a specific embodiment, the shaft and handle are molded as a single unit.

The shaft and other parts of the retractor may be made of any material suitable for use in surgery, especially for human surgery. Generally, a material is suitable for surgery as long as it is not toxic or reactive (e.g., causing an allergy or undesirable chemical reaction) for a particular person, organism, or procedure.

Further, in a specific implementation, the material of the retractor is not reflective or minimally reflective. This will ensure that more of the light which is transmitted into the tissue is received back at the detectors, instead of being reflected off the retractor. For example, the retractor may be coated with an antireflective material (such as a black oxide coating) to make it less reflective than the original starting material. Or the retractor may be processed (e.g., bluing, anodizing, or oxiding) to make the surface less reflective than the original starting material. The retractor may be colored (e.g., black flat color), or finished (e.g., matte finish), or textured (e.g., bead-blasted finish) to reduce reflectivity. Another benefit of reducing reflectivity of the retractor is that there will be less glare for the surgeon when operating.

In another specific implementation, the material of the retractor is not electronically conductive or has reduced electrical conductivity compared to the original starting material. Because the retractor is used to retract nerves, it may not be desirable to shock the nerves with electrostatic energy accidentally. The retractor may be made from material that is not conductive such as a ceramic, plastic, or resin. Or the retractor may include insulating material inserted between the tip (which touches the nerve) and the point at which the surgeon holds the retractor (or other portions of the retractor). For example, the handle may include rubber or the surgeon may wear nonconductive gloves, and this will stop accidental electrostatic discharges.

In another specific implementation, the material of the retractor is not thermally conductive or has reduced thermal conductivity compared to the original starting material. Because the retractor is used to retract nerves, temperature changes in the retractor can be propagated to the nerve quite quickly. It is generally desirable not to thermally heat the nerve or else it may become damaged. So, the retractor may be made from material that is not thermally conductive such as a ceramic, plastic, or resin. Or the retractor may include thermally insulating material inserted between the tip (which touches the nerve) and other portions of the retractor.

In a specific embodiment, the shaft is metal, such as steel, stainless steel, or surgical stainless steel, or combinations of these and other suitable materials. Some other metals that may be used include gold, silver, rhodium, titanium, tungsten, molybdenum, and aluminum. The shaft may be an alloy of two or more elements (e.g., iron, carbon, chromium, molybdenum, and nickel). In other embodiments, the shaft may be made of plastics, ceramics, or composites (e.g., carbon fiber). The shaft may also include a combination of materials such as steel surrounded by shrink-wrap tubing.

In a specific embodiment, the shaft is a solid rod, and one or more fiber optic cables (e.g., four fiber optic cables) are run along at least some portion of the length of the shaft. The ends of the fiber optic cable terminate at one or more openings in the tip so that light can be transmitted into the nerve (or other tissue) and received from the nerve. The opposite ends of the fiber optic cable may terminate at the connector on the cable, which will be connected to the console (see, e.g., FIG. 3). The shaft and fiber optic cables can be bound together using a jacket such as heat-shrink tubing.

The handle may be made of any material such as plastic, metal (e.g., steel, aluminum, and titanium), ceramics, composites (e.g., carbon fiber), or rubber, or combinations of these. The handle may be ergonomically designed so that it is comfortable for a user to hold. Some examples of ergonomic designs include contoured surfaces as shown in FIG. 5 and the use of soft materials (e.g., rubber). The handle may also be textured (e.g., knurled) so that the tool is less likely to slip from the user's hand.

Typically, the handle is at an angle relative to the shaft. For example, an axis 535 passes longitudinally through the handle while an axis 538 passes longitudinally through at least a portion the shaft. The two axes form an angle 542. In a specific implementation, angle 542 is 110 degrees. However, angle 542 may be 90 degrees (i.e., a right-angle), less than 90 degrees (i.e., an acute angle), or greater than 90 degrees (i.e., an obtuse angle). Angle 542 typically ranges from about 90 degrees to about 160 degrees. This includes, for example, 95, 100, 110, 115, 120, 125, 130, 135, 140, 145, 150, 155, 160, or more than 160 degrees. However, in an embodiment, the retractor has no angular difference between the handle and shaft (i.e., angle 542 is 180 degrees) and retractor is a straight puller.

The various angles allow the user to select that angle that the user is most comfortable working with. For example, one user may prefer a tissue retractor oximeter with a 90-degree angle because that user finds that at that angle, the retractor is not sticking up towards the microscope interfering with vision and with the operating surgeon. In other implementations the shaft may be bendable by the user who can then shape the shaft into any angle or configuration. In yet another implementation, the shaft may include two or more pieces that are pivotly connected such as via screws and nuts. This too allows the user to determine and set the desired angle and configuration.

In a specific embodiment, the shaft and handle may be detached and reattached by the user. This allows, for example, the user to select an angle for the retractor and use the same handle without having to purchase a whole new retractor.

In a specific implementation, the retractor has a shaft length L1 of about 120 millimeters and a handle length L2 of about 120 millimeters. However, these dimensions may vary widely depending on the application.

Figure 6A:
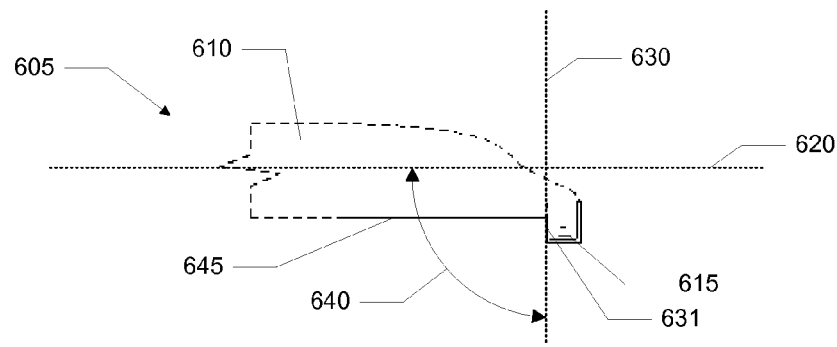
FIG. 6A shows a right-hand side view of a tip connected to the shaft of a tissue retractor oximeter.

FIG. 6A shows a right-hand side view of a tip 605. A left-hand side view of the tip is a mirror image of what is shown in FIG. 6A. Tip 605 is connected to a distal end 610 of the shaft. The tip includes a retractor portion or blade 615 and a bottom surface 645. The blade is at an angle relative to the shaft and to the bottom surface.

Blade surface 631 may be flat, as shown, or angled (e.g., concave or convex) or have another contour (e.g., ogee, French curve, arch, or hook) as desired for the particular operation or intended use. The various contours on the blade surface may be part of a blade that also has one or more contours in other dimensions or planes.

Figure 6B:
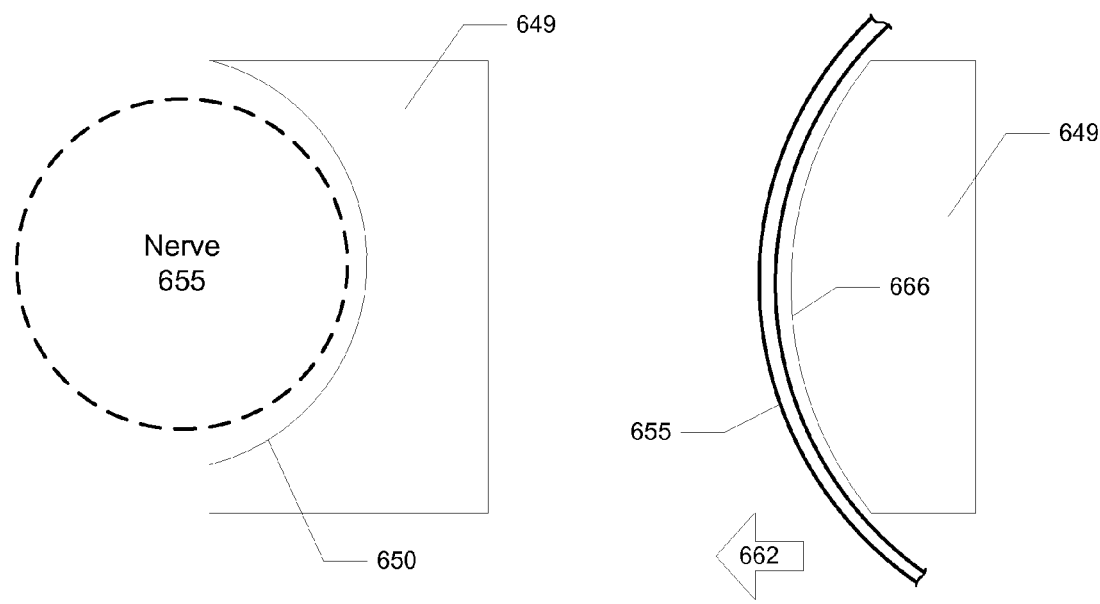
FIG. 6B shows a side view of an embodiment of a blade with a concave surface against a nerve.
Figure 6B:
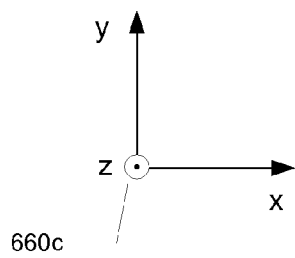

FIG. 6B shows, for example, a side view of a blade 649 having a concave blade surface 650. The concave blade surface is shown against a nerve 655. The view shown is from a z-axis 660c. In a specific implementation, the concave blade surface has a constant radius as shown, but may also have a varying radius in other implementations.

The concave blade surface allows the nerve to be gently cradled as it is retracted. The stresses around the perimeter of the nerve may be more evenly distributed which may help prevent the nerve from traumatically creasing, folding, or compressing.

In a specific implementation, the blade surface may also have a textured surface. For example, the surface may include multiple nubs, bumps, ribs, or protrusions. These surface features may help to lift portions of the nerve away from the blade surface so as to minimize any crushing of blood vessels running alongside the nerve or to promote aeration of the nerve.

In another implementation, the blade surface may have multiple holes to promote, for example, aeration of the nerve while it is being retracted.

Figure 6C:
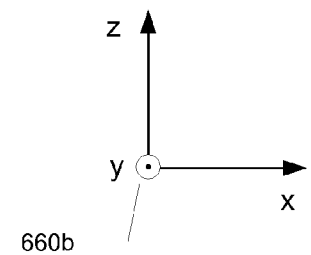
FIG. 6C shows a top view of an embodiment of a blade with a convex side against a nerve.

FIG. 6C shows a top view of blade 649 against nerve 655. The view shown is from a y-axis 660b. An arrow 662 indicates the direction of retraction. Blade 649 may have a convex side 666 in addition to concave surface 650 shown in FIG. 6C. Like the concave surface, the convex side has similar benefits. That is, as the nerve is being retracted, there will be less pinching (i.e., high pressure points or relatively higher force per unit area) at the outermost points of the arc or crescent. An arc shape generally reduces the number of high stress points when retracting a nerve.

Referring now to FIG. 6A, bottom surface 645 may be flat, as shown, or have another contour as desired for the particular operation or intended use. For example, the bottom surface may have a concave region to similarly cradle the nerve and distribute stress as shown in FIG. 6B. The bottom surface may also be textured (e.g., nubs, bumps, ribs, and protrusions) to lift portions of the nerve away from the bottom surface so as to minimize any crushing of blood vessels running alongside the nerve or to promote aeration of the nerve.

An axis 620 passes longitudinally through the shaft. In this specific implementation, bottom surface 645 is a flat plane that is parallel to axis 620, but this is not necessarily the case for other implementations of the retractor (see below).

An axis 630 passes through a blade surface 631 and intersects axis 620. In this specific implementation, blade surface 631 is flat, but this is not necessarily the case for other implementations of the retractor. The blade surface is angled (i.e., angle 640) relative bottom surface 645 and axis 620.

In a specific implementation, angle 640 is about 90 degrees. However, as discussed above, the specific angle may vary. Typically, angle 640 ranges from about 90 degrees to about 179 degrees. For example, the angle may be about 100, 110, 120, 130, 135, 140, 150, 160, 170, or more than 179 degrees, such as 180 degrees. In other implementations, the angle is less than 90 degrees.

The various angles accommodate the preferences of different users and intended uses for the retractor. For example, during spinal surgery the user uses the blade to retract the nerve off to one side so that the surgeon can work on the disc without damaging the nerve. Some users may prefer to retract the nerve using a downward motion and then pulling the nerve to the side. For these users, a 90-degree blade may be appropriate.

Other users may prefer to retract the nerve using both a downward and sideways motion. For these users, a blade with an angle to the shaft greater than 90 degrees, such as 130 degrees may be more appropriate than a blade having a 90-degree angle. Further, the angle of the blade may be helpful in preventing too much force from being applied to a nerve, which may possibly damage the nerve or tissue.

Further, as shown above, the blade is angled relative to the bottom surface of the tip. But this angle is not necessarily the same angle as between the blade and the axis of the shaft. For example, in some implementations of the invention (which are not shown), the bottom surface of the tip may be perpendicular (or at another angle) relative to the axis of the shaft. Then, the blade would be angled relative to the bottom surface, but parallel to the axis of the shaft.

The blade is angled relative to the bottom surface. In a specific implementation, this angle is about 90 degrees. However, this angle may range from about 90 degrees to about 179 degrees. For example, this angle may be about 100, 110, 120, 130, 135, 140, 150, 160, 170, or more than 179 degrees, such as 180 degrees. In other implementations, the angle is less than 90 degrees.

Figure 7:
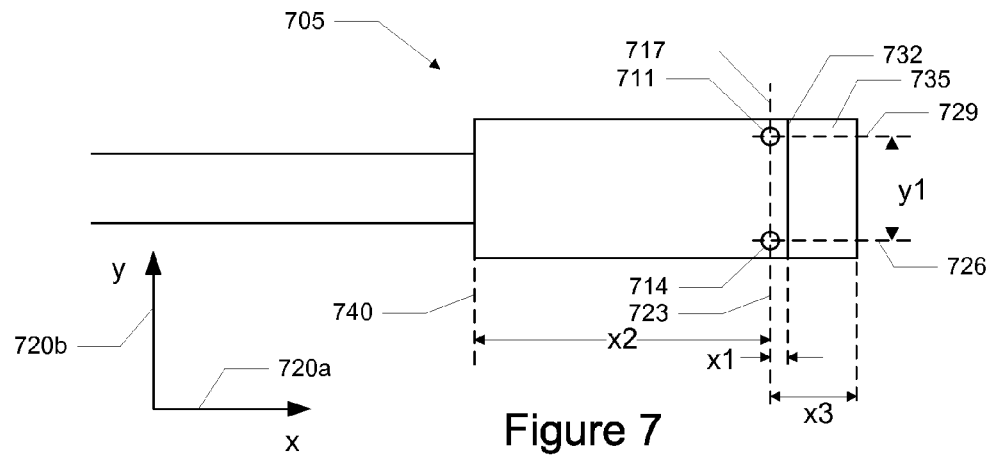
FIG. 7 shows a bottom view of a tip with a single light source and single detector symmetrical array.

FIG. 7 shows a bottom view of a tip 705 with two openings, a single light source and single detector in a symmetrical array. In the implementation shown in FIG. 7, the tip has two openings. A first opening includes a source structure 711. A second opening includes a detector structure 714.

The source and detector structures generally include optical fiber that are used to measure oxygen saturation levels in tissue, such as a nerve. In an implementation, optical fiber is used having a diameter of about 1 millimeter, but other diameter fibers may be used, including 0.5 millimeter, 0.75 millimeter, 2 millimeters, 3 millimeters, 4 millimeters, 5 millimeters, and larger sizes.

The source structure typically includes an end of a first optical fiber where the opposite end of the first optical fiber is connected to a light source. The detector structure typically includes an end of a second optical fiber where the opposite end of the second optical fiber is connected to a photodetector.

In a specific implementation, the source and detector structures are in a symmetrical arrangement. For example, each source and detector structure has a reference point. The reference point may be the centers of the sources and detectors if, for example, the sources and detectors have circular shapes. Alternatively, the reference point may be defined as some other point, so long as the definition is consistent among the sources and detectors.

Lines 717 and 723 pass through the source and detector structures. Line 717 is parallel to a y-axis 720b and passes through the reference point of source structure 711. Line 723 is parallel to y-axis 720b and passes through the reference point of detector structure 714. Lines 717 and 723 are coincident. That is, source structure 711 is in a symmetrical arrangement with respect to detector structure 714.

A line 726 is parallel to an x-axis 720a and passes through the reference point of the detector structure. A line 729 is parallel to x-axis 720a and passes through the reference point of the source structure. Source structure 711 and detector structure 714 are separated by a distance y1 between lines 726 and 729.

The separation between the source and detector structures may vary widely. By way of example, distance y1 is about 1.5 millimeters. A smaller distance y1 helps to contribute to a smaller tip size. Smaller tip sizes are generally desirable because they allow the use of smaller incisions. In turn, a smaller incision allows for faster healing and less scarring. Patients may also experience fewer infections.

However, in another implementation, distance y1 is about 5 millimeters. Distance y1 generally ranges from about 1.5 millimeters to about 5 millimeters. For example, distance y1 may be about 1.5, 2, 2.5, 3, 3.5, 4, 4.5, 5, or more than 5 millimeters. In other implementations, distance y1 may be less than 1.5 millimeters.

Larger source-detector separations may allow, for example, the detector structures to detect light after the light has penetrated deeper into the tissue.

In a specific implementation where fiber optic cables are included, the size of the fiber optic cable may vary. In a specific implementation, where fiber optic cables having circular cross sections are used, the diameter of a fiber optic cable end at the source structure, detector structure, or both is approximately 0.5 millimeters, but may range from about 0.5 millimeters to about 3 millimeters. For example, the diameter may be about 0.5, 1, 1.5, 2, 2.5, 3, or more than 3 millimeters. In other implementations, the diameter of the fiber optic cable may be less than 0.5 millimeters.

Generally, the diameter of the fiber optic cable and corresponding opening will be about the same. Smaller openings allow, for example, smaller tips. Larger openings, allow, for example, more light to be transmitted into the tissue, and received from the tissue.

A distance x1 is between line 723 and an edge 732. That is, the source and detector structures may be offset by distance x1 from edge 732. Edge 732 marks the base of a retractor portion or blade 735. The source and detector structures are typically placed close to edge 732 such that distance x1 is at least about 0.5 millimeters. However, distance x1 may vary from about 0.5 millimeters to about 3 millimeters depending on the application.

Typically, the source and detector structures are located closer to the retractor portion as opposed to the distal end of the shaft. For example, a line 740 that is parallel to the y-axis passes through the distal end of the shaft.

A distance x2 is between lines 740 and 717. Generally, distance x2 will be greater than distance x1. In a specific implementation, distance x2 is about 4.8 times greater than distance x1. However, distance x2 may range from about 3 to about 6 times greater than distance x1. For example, distance x2 may be 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, or more than 5.5 times greater than distance x1. In other implementations, distance x2 may be less than 3 times greater than distance x1.

The variations of the relationship between distance x2 and distance x1 reflects the varying dimensions of a nerve or other linear tissue. For example, the diameter of a nerve may vary from patient-to-patient. It may also vary along the length of a nerve. The diameter of a nerve may range from about 1 millimeter to about 5 millimeters. For example, the nerve root in the lower back of a typical adult is about 4 millimeters in diameter. Because the nerve is typically retracted using the blade, locating the source and detector structures near edge 732 allows light to be transmitted from the source structure into the nerve and then received by the detector structure.

Generally, distance x1 will be proportional to the size of the nerve. That is, smaller nerves will result in a smaller distance x1 while larger nerves will result in a larger distance x1. Since nerves generally have circular cross-sections, this dimensional relationship helps to ensure, for example, that the source and detector structures are placed over the thickest part of the nerve, i.e., over the diameter of the nerve, when the nerve is pulled by the hook.

For example, where the nerve is small, such as the nerve of a child, the source and detector structures may be located closer to edge 732 so that the source and detector structures will be located above the nerve. Thus, light can be transmitted into the nerve and received from the nerve. Where, however, the nerve is large, such as the nerve of an adult, the source and detector structures may be located further away from edge 732.

Typically, the source and detector structures are located along one or more axes that are parallel to the longitudinal edge of the retractor portion. This allows, for example, measurements of linearly-shaped tissue such as a nerve. For example, line 717, which passes through the source and detector structures, is parallel to edge 732 of the retractor portion. During use, the nerve is typically situated against edge 732. The longitudinal axis of the nerve is then parallel to edge 732. Locating the source and detector structures along axes parallel to edge 732 helps to ensure that the nerve will be located below the source and detector structures.

A distance x3 is from line 723 to an outside edge of the blade. In a specific embodiment, distance x3 is about 1.75 millimeters. However, distance x3 may vary depending on the application including, for example, the material that the retractor is made of. For example, a material with a relatively high strength may allow for a thin blade (i.e., a shorter distance x3). However, a material with a lower strength may require a thicker blade (i.e., a longer distance x3) so that the blade is more durable, making harder to break or bend.

In a specific embodiment, the source and detector structures may be located on the blade. The source and detector structures may have similar positions, configurations, arrangements, shapes, designs, measurements, and spacings as they would have if placed on the bottom surface of the tip as discussed in this application. Furthermore, a specific embodiment may include a combination of source structures, detector structures, or both that are located on the blade and bottom surface of the tip.

One advantage of locating the source structures, detector structures, or both on the blade is that it may allow for a measurement (e.g., oxygen saturation measurement) to be made without the tissue having to contact or be positioned close to the bottom surface of the tip. For example, there may be some situations where the user is unable to fully insert the blade into the incision such that when the tissue is retracted the sensors on the bottom surface are close enough to the retracted tissue that a measurement can be made. However, sensors located on the blade may be close enough to the tissue to make the measurements.

In another implementation, the arrangement of sources and detectors is asymmetrical. An asymmetrical arrangement of sources and detectors is discussed in U.S. Pat. No. 7,355,688, which is incorporated by reference. Any of the asymmetrical arrangements of sources and detectors discussed in that patent is applicable to the sources and detectors in this application.

Figure 8:
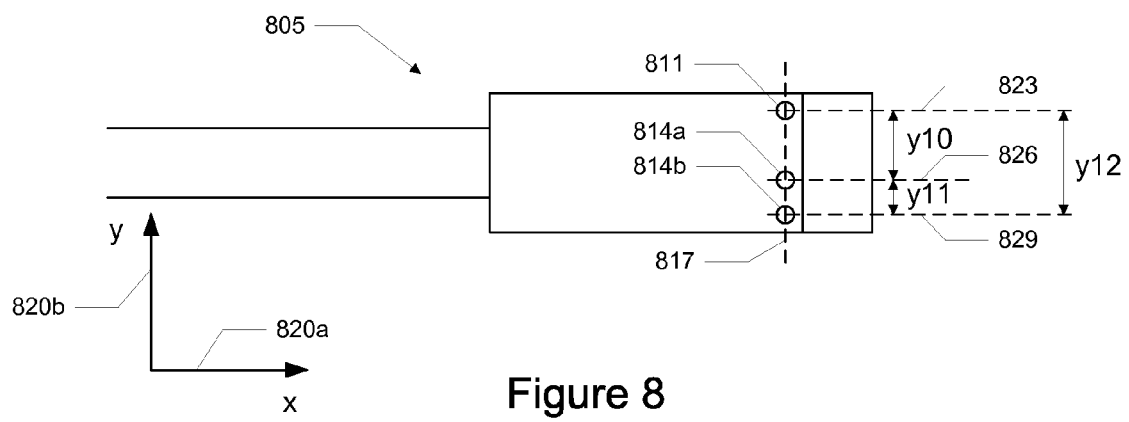
FIG. 8 shows a bottom view of a tip with a single light source and two detector asymmetrical array.

For example, FIG. 8 shows a bottom view of a tip 805 with three openings, one light source and two detectors in an asymmetrical array. In the implementation shown in FIG. 8, the tip has three openings arranged on a line. A first opening includes a source structure 811. Second and third openings include detector structures 814a and 814b, respectively.

A line 817 which is parallel to a y-axis 820b passes through the reference point for each of the source and detector structures. A line 823 which is parallel to an x-axis 820a passes through the reference point of source structure 811. A line 826 which is parallel to the x-axis passes through the reference point of detector structure 814a. A line 829 which is parallel to the x-axis passes through the reference point of detector structure 814b.

The asymmetrical source and detector array of FIG. 8 includes source structure 811 and detector structure 814b, with detector structure 814a interposed between source structure 811 and detector structure 814b. Source structure 811 and detector structure 814b are located at opposite ends of the array, while detector structure 814a is located in a middle, but off-center portion of the array.

For example, a distance y10 is between lines 823 and 826. A distance y11 is between lines 826 and 829. Distance y10 is different from distance y11. Although distance y10 is shown as being greater than distance y11, it should be appreciated that distance y11 may instead be greater than distance y10. The difference between distance y10 and distance y11 is generally characteristic of the offset arrangement, or substantially unbalanced arrangement of the source structure relative to the detector structures.

A distance y12 is between lines 823 and 829. In a specific implementation, distance y11 is about one-third of the distance y12 and distance y10 is about two-thirds of the distance y12. For example, if y12 is 5 millimeters then y11 is 5/3 millimeters and y10 is 10/3 millimeters (i.e., 2/3*5 millimeters is 10/3 millimeters).

However, other implementations may include a symmetrical source-detector arrangement. For example, distance y10 may equal distance y11.

Figure 9:
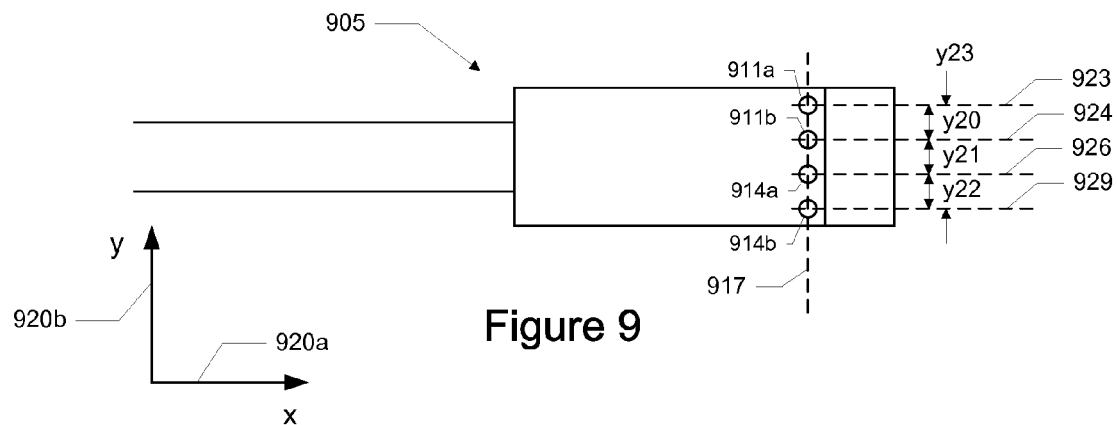
FIG. 9 shows a bottom view of a tip with a two light source and two detector symmetrical array.

FIG. 9 shows a bottom view of a tip 905 with four openings, two light sources and two detectors in a symmetrical array. In the implementation shown in FIG. 9, the tip has four openings arranged on a line. First and second openings include source structures 911a and 911b, respectively. Third and fourth openings include detector structures 914a and 914b, respectively.

A line 917 which is parallel to a y-axis 920b passes through the reference point for each of the source and detector structures. A line 923 which is parallel to an x-axis 920a passes through the reference point of source structure 911a. A line 924 which is parallel to x-axis 920a passes through the reference point of source structure 911b. A line 926 which is parallel to the x-axis passes through the reference point of detector structure 914a. A line 929 which is parallel to the x-axis passes through the reference point of detector structure 914b.

The two light source and two detector array of FIG. 9 includes source structure 911a and detector structure 914b located at opposite ends of the array, while source structure 911b and detector structure 914a are interposed between source structure 911a and detector structure 914b. That is, the arrangement shown in FIG. 9 provides the furthest separation between a source and detector structure (i.e., 911a and 914b) by locating them on opposite ends of the array.

Separating source structure 911a and detector structure 914b as far as possible has advantages over other arrangements that may locate the source structures on opposite ends of the array with the detector structures interposed between. One advantage is that the light emitted from source structure 911a can travel deeper into the tissue before it is received by detector structure 914b. Another advantage is that the tip may be constructed with a very small size and therefore can be used in clinical applications where smaller instruments are advantageous because only a small incision is required to use them. Applications include, for example, spinal nerve root oxygenation measurement and monitoring in digit replantation.

In a specific implementation, the two-light-source and two-detector array is symmetrical. That is, the spacing between adjacent sources and detectors is equal. For example, a distance y20 is between lines 923 and 924. A distance y21 is between lines 924 and 926. A distance y22 is between lines 926 and 929. A distance y23 is between lines 923 and 929.

In a specific implementation, distances y20, y21, and y22 are the same. In a specific implementation, distances y20, y21, and y22 are each one-third the distance y23. For example, if y23 is 5 millimeters then y20, y21, and y22 are all 5/3 millimeters.

Figure 10:
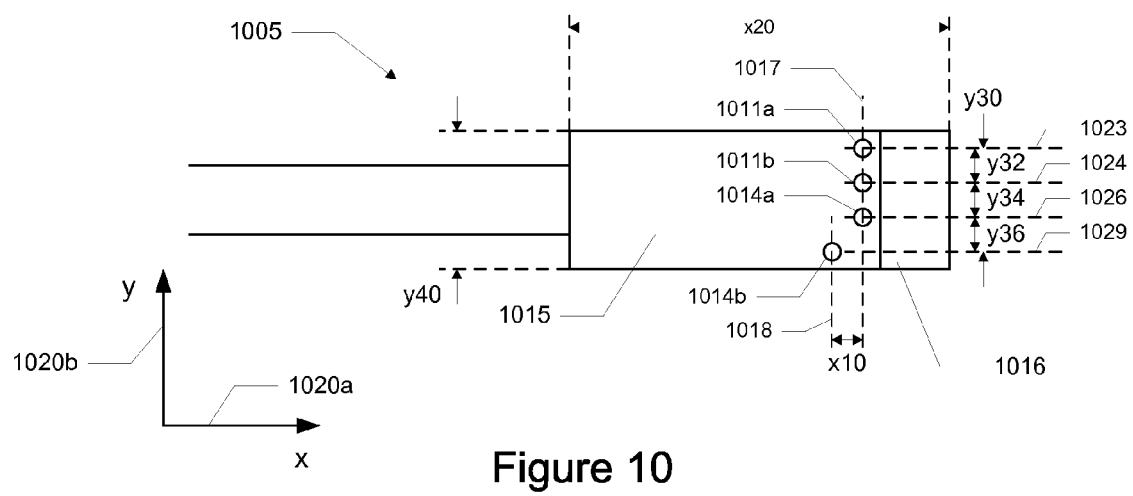
FIG. 10 shows a bottom view of a tip with a two light source and two detector asymmetrical array.

FIG. 8 described a lack of symmetry in the positioning of source and detector structures such that distances between source and detector structures varied relative to a y-axis. However, a lack of symmetry may instead or additionally have a lack of symmetry relative to an x-axis. Referring next to FIG. 10, a tip that includes a detector structure in an offset arrangement relative to a set of source structures and a detector structure will be described.

FIG. 10 shows a bottom view of a tip 1005 with four openings, where at least one of the openings is not aligned or asymmetrical with the other openings. In this figure, there is one opening that is not aligned with the openings. In another implementation, there are two openings that are not aligned with the other openings. In another implementation, there are at least three openings that are not aligned to each other. In another implementation, there are at four openings that are not aligned to each other.

A specific implementation of the figure has two light source and two detectors in an asymmetrical array. In the implementation shown in FIG. 10, the tip has four openings with three openings arranged on the same line and a fourth opening arranged offset from the line. First and second openings include source structures 1011a and 1011b, respectively. Third and fourth openings include detector structures 1014a and 1014b, respectively. The tip also includes a bottom surface 1015 and a retractor portion or blade 1016.

A line 1017 which is parallel to a y-axis 1020b passes through the reference point for source structures 1011a and 1011b and detector structure 1014a. A line 1018 which is parallel to y-axis 1020b passes through the reference point for detector structure 1014b.

A line 1023 which is parallel to an x-axis 1020a passes through the reference point of source structure 1011a. A line 1024 which is parallel to x-axis 1020a passes through the reference point of source structure 1011b. A line 1026 which is parallel to the x-axis passes through the reference point of detector structure 1014a. A line 1029 which is parallel to the x-axis passes through the reference point of detector structure 1014b.

A distance y30 is between lines 1023 and 1029. A distance y32 is between lines 1023 and 1024. A distance y34 is between lines 1024 and 1026. A distance y36 is between lines 1026 and 1029.

Lines 1017 and 1018 although parallel to the y-axis are not coincident. That is line 1017 is offset from line 1018 by a distance x10 along the x-axis, i.e., there is a lack of symmetry with respect to the x-axis. In a specific implementation x10 is about 0.5 millimeters. However, x10 may range from about 0.1 millimeters to about 2.5 millimeters. For example, x10 may be 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5 or more than 2.5 millimeters. In other implementations, x10 may be less than 0.1 millimeters.

As a further example, in an asymmetrical arrangement, the sources and detectors are arranged so there is a first distance between a first source structure (e.g., 1011a) and a first detector structure (e.g., 1014a) and a second distance between the second source structure (e.g., 1011b) and a second detector structure (e.g., 1014b), where the first and second distances are not equal.

For example, in a specific implementation, the distance along the y-axis between adjacent sensors is $$\frac{n}{(m-1)},$$

where n is the distance along the y-axis between the furthest source and detector pair and m is the number of sensors. Thus, in a specific implementation including four sensors and a y-axis distance of 5 millimeters between the furthest source and detector pair, the y-axis distance between adjacent sensors is 5/3 millimeters $$\left(\text{i.e., } \frac{5 \text{ millimeters}}{(4-1)} = \frac{5}{3} \text{ millimeters}\right).$$

In this example then, the first distance (i.e., source structure 1011a to detector structure 1014a) is 10/3 millimeters (i.e., 3.3 millimeters). The second distance (i.e., source structure 1011b to detector structure 1014b) is 3.4 millimeters, where x10 is 0.5 millimeters (i.e., second distance= $\sqrt{(0.5)^2+(3.3)^2}=3.4$).

The bottom surface is generally planar with one or more openings through which light is transmitted into the tissue and received from the tissue. However, in other implementations, the bottom surface may not be planar. For example, the bottom surface may have a convex surface, a concave surface, or both convex and concave regions.

In a specific implementation, the bottom surface may have the shape of a rectangle. However, this is not always the case. The bottom surface may have any shape. For example, in an implementation, the bottom surface may have the shape of a different type of polygon such as a square, rectangle, triangle, and parallelogram, or have a shape composed of curved line segments (e.g., oval, ellipse, and crescent), or combinations of these (e.g., semicircle).

Typically, the surface area of the bottom surface will be larger than the surface area of the openings. For example, the surface area of the bottom surface may be about two-hundred and fifty to about three-hundred and fifty times greater than the combined surface area of the openings. In other implementations, the surface area of the bottom surface will be less than or equal to the surface area of the openings.

In a specific implementation, the bottom surface has a length x20 and a width y40. In a specific implementation, such as a single source and single detector array, the bottom surface has a width of about 3 millimeters and a length of about 5 millimeters. In another implementation, such as with additional sources and detectors (e.g., two-source and two-detector array), the bottom surface may have a greater width such as 8 millimeters. Table A below shows dimensions-length x20 (FIG. 10), width y40 (FIG. 10), and thickness y44 (FIG. 12)—for various implementations of the invention, and also a range of dimensions. However, it should be noted that these dimensions may vary greatly depending upon the application.

TABLE A

| Dimension | First Implementation (millimeters) | Second Implementation (millimeters) | Third Implementation (millimeters) | Range of Dimensions (millimeters) |
| --- | --- | --- | --- | --- |
| Length (x20) | 5 | 17.5 | 17.5 | 2.5-20 |
| Width (y40) | 3 | 8 | 8 | 2-20 |
| Thickness (y44) | 2 | 3 | 5 | 2-5 |

In a specific implementation, an attenuation ratio is used to determine tissue oxygenation ($StO_2$), hemoglobin concentration (Hgb), or both. The attenuation ratio is the ratio of light attenuation emitted by a source and received by a detector at a wavelength to that of another wavelength. The attenuation ratio can then be generally expressed in the following equation:

$$R(S, D) = \frac{U^{\lambda_1}(S, D)}{U^{\lambda_2}(S, D)} \qquad (1)$$

where $\mu^{\lambda_i}(S,D)$ for i=1, 2, is the light intensity received by the detector when the source is on at wavelength $\lambda_i$.

In a specific implementation, light is emitted from the source structures at two different wavelengths including, for example, 690 nanometers and 830 nanometers. For the source-detector array shown in FIG. 10, there are four source-detector pairs including: $(S_1, D_1)$, $(S_1, D_2)$, $(S_2, D_1)$, and $(S_2, D_2)$. $S_1$ and $S_2$ correspond to source structures 1011a and 1011b, respectively. $D_1$ and $D_2$ correspond to detector structures 1014a and 1014b, respectively.

For each source-detector pair $(S_i, D_j)$ for i=1, 2, there are two optical measurements including: $U^{690}(S_i,D_j)$ and $U^{830}(S_i,D_j)$. The attenuation ratio is thus defined as:

$$R(S_i, D_j) = \frac{U^{690}(S_i, D_j)}{U^{830}(S_i, D_j)} \qquad (2)$$

In the automatic error-cancellation or self-calibration scheme, the system factors such as source intensity, detector gain, and loss of light in the optical fibers and connectors are cancelled automatically. The automatic error-cancellation scheme is discussed in more detail as equations 5a and 5b in U.S. patent application 6,597,931, which is incorporated by reference.

For the linear sensor array, such as that shown in FIG. 10, one can form the following four quantities independent of these system factors:

$$\begin{cases} U^{(4)}(690, 690) = \dfrac{U(S_1^{690}, D_1)U(S_2^{690}, D_2)}{U(S_1^{690}, D_2)U(S_2^{690}, D_1)}, \\[4pt] U^{(4)}(690, 830) = \dfrac{U(S_1^{690}, D_1)U(S_2^{830}, D_2)}{U(S_1^{690}, D_2)U(S_2^{830}, D_1)}, \\[4pt] U^{(4)}(830, 690) = \dfrac{U(S_1^{830}, D_1)U(S_2^{690}, D_2)}{U(S_1^{830}, D_2)U(S_2^{690}, D_1)}, \\[4pt] U^{(4)}(830, 830) = \dfrac{U(S_1^{830}, D_1)U(S_2^{830}, D_2)}{U(S_1^{830}, D_2)U(S_2^{830}, D_1)} \end{cases} \qquad (3)$$

For the attenuation ratio method, one needs to take the ratios of these four quantities:

$$\begin{cases} R_1 = \dfrac{U^{(4)}(690, 690)}{U^{(4)}(690, 830)} = \dfrac{R(S_2, D_2)}{R(S_2, D_1)}, \\[4pt] R_2 = \dfrac{U^{(4)}(690, 690)}{U^{(4)}(830, 690)} = \dfrac{R(S_1, D_1)}{R(S_1, D_2)}, \\[4pt] R_3 = \dfrac{U^{(4)}(690, 690)}{U^{(4)}(830, 830)} = \dfrac{R(S_1, D_1)R(S_2, D_2)}{R(S_1, D_2)R(S_2, D_1)} = R_1 R_2, \\[4pt] R_4 = \dfrac{U^{(4)}(690, 830)}{U^{(4)}(830, 690)} = \dfrac{R(S_1, D_1)R(S_2, D_1)}{R(S_1, D_2)R(S_2, D_2)} = \dfrac{R_1}{R_2}, \\[4pt] R_5 = \dfrac{U^{(4)}(690, 830)}{U^{(4)}(830, 830)} = \dfrac{R(S_1, D_1)}{R(S_1, D_2)} = R_2, \\[4pt] R_6 = \dfrac{U^{(4)}(830, 690)}{U^{(4)}(830, 830)} = \dfrac{R(S_2, D_2)}{R(S_2, D_1)} = R_1 \end{cases} \qquad (4)$$

Note that $R_1$ depends only on $S_1$, $R_2$ depends only on $S_2$, and $R_4$ depends on both $S_1$ and $S_2$. Also note that $R_3$ can serve as a measure of signal quality, and $R_5$ and $R_6$ are not independent.

The following equation may be used without the self-calibration scheme. The attenuation ratio may be related to $StO_2$. $StO_2$ may be proportional to the attenuation ratio. Assuming a linear relation we have the equation:

$$StO_2(S_i, D_j) = kR(S_i, D_j) + b \qquad (5)$$

where $R(S_i, D_j)$ is defined in equation (2), and k and b may be constants. We empirically take k=30 and b=0. If further $StO_2$ calibration is required for each individual sensor then the calibration data may be stored in a chip embedded in the sensor. Theoretically, the pair $(S_1, D_2)$ should be most sensitive to $StO_2$ change. The calibration factors (k,b) in equation (5) are console- and probe-dependent because the self-calibration scheme is not used in the $StO_2$ calculation and therefore system factors have not been cancelled. This complexity may be avoided by recording the ratio $$\frac{U^{690}(S_i, D_j)}{U^{830}(S_i, D_j)}$$

when a console-probe combination is used for the first time.

Furthermore, to avoid this problem, one may use the attenuation ratio method under the self-calibration scheme as described below.

With self-calibration, the self-calibrated attenuation ratio may be better than that without self-calibration for estimating the oxygenation. We assume:

$$StO_2(m) = k'R_m + b', \; m=1, 2, 4 \qquad (6)$$

m=4 if both $S_1$ and $S_2$ are involved. m=1 if only $S_1$ is involved. m=2 if only $S_2$ is involved. The calibration factors (k', b') in equation (6) are now independent with respect to the console and probe. We empirically take k=100 and b=−30%.

Under a Monte Carlo simulation, when a light source is on, the light received by a detector is related to the source-detector separation by $$U(\rho) \approx \frac{e^{-\rho\sqrt{6\mu_{\text{eff}}}}}{\rho^2},$$

where $\mu_{\text{eff}}$ is the attenuation coefficient of the medium. A Monte Carlo simulation technique is discussed in *Approximate Theory of Photon Migration in a Two-layer Medium*, by H. Taitelbaum, S. Havlin, and G. H. Weiss, Applied Optics, 28(12), page 2245 (1989), which is incorporated by reference. In the auto-calibration or error-cancellation scheme, $$U^{(4)} \approx G_1' e^{-G_2'\sqrt{6\mu_{\text{eff}}}},$$

where $G'_1$; and $G'_2$ are probe-geometry dependent. Assuming $\mu'_s$ is independent of wavelength, we have $$U^{(4)} \approx G_1' e^{-G_2''\sqrt{\mu_a}}.$$

The absorption coefficient is then calculated according to the following equation:

$$\mu_a = (G_1 + G_2 \ln U^{(4)})^2 \qquad (7)$$

In the current algorithm, we take $G_1=0.5$ and $G_2=1$. Using the $\mu_a$ at the two wavelengths, Hgb is calculated in terms of $\mu_a$ at the two wavelengths.

The quantity $R_3$ in equation (4) can serve as a measure of signal quality, i.e., we define the signal quality factor by:

$$Q = R_3 \qquad (8)$$

$$= \frac{U(S_1^{690}, D_1)U(S_2^{690}, D_2)}{U(S_1^{690}, D_2)U(S_2^{690}, D_1)} \bigg/ \frac{U(S_1^{830}, D_1)U(S_2^{830}, D_2)}{U(S_1^{830}, D_2)U(S_2^{830}, D_1)}$$

$$= \frac{U_1 U_6 U_{10} U_{13}}{U_2 U_5 U_9 U_{14}}$$

Additional detail on signal quality factors is discussed in U.S. patent application Ser. No. 11/162,380, filed Sep. 8, 2005, which is incorporated by reference.

It should also be appreciated that these equations may be applied to symmetrical source and detector arrangements such as that arrangement shown in the example of FIG. 9. The self-calibration scheme may include equations discussed in U.S. Pat. Nos. 6,516,209, 6,735,458, and 6,078,833, and *New Optical Probe Designs for Absolute (Self-Calibrating) NIR Tissue Hemoglobin Measurements*, Proc. SPIE 3597, pages 618-631 (1999), which are incorporated by reference. The attenuation ratio method may also include techniques discussed in U.S. Pat. No. 6,587,701, which is incorporated by reference.

When the tip has two source openings and two detector openings, in a specific implementation, $StO_2$ is calculated using equation (6). That is, the self-calibration or auto-calculation scheme is used.

When the tip has one source opening and one detector opening, in a specific implementation, $StO_2$ is calculated using equation (5). That is, without using the self-calibration or auto-calculation scheme. The weighted average over source-detector pairs is not necessary because there is only one source-detector pair.

When the tip has one source opening and two detector openings, in a specific implementation, $StO_2$ is calculated using equation (5). The weighted average is over the two source-detector pairs.

Figure 11:
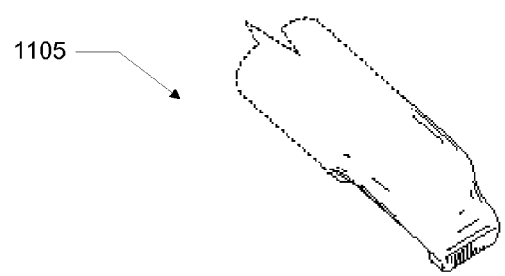
FIG. 11 shows a perspective view of a first embodiment of a tip.

FIG. 11 shows a perspective view of a first embodiment of a tip 1105. In an implementation, the fiber optic cables that run to the sensor openings on the bottom surface of the retractor are encased in or sealed using an epoxy, adhesive, resin, plastic, or similar material or compound. The epoxy (or other material) holds the fibers in place, prevents damage to the fibers, and prevents detaching of the fibers from the sensor openings during use. The shape of the epoxy or other material may be sculpted as shown to facilitate ease in use of the device.

Figure 12:
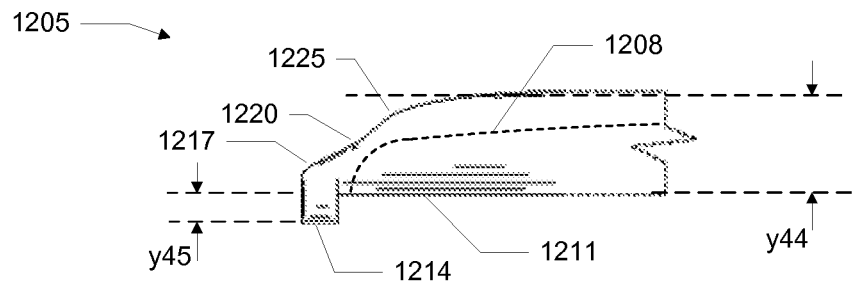
FIG. 12 shows a left-hand side view of the first embodiment of a tip.

FIG. 12 shows a left-hand side view of a first embodiment of a tip 1205. The tip includes one or more fiber optic cables 1208 (partial view), a bottom surface 1211, and a retractor portion or blade 1214.

In a specific implementation, the one or more fiber optic cables are encased in epoxy or molded within a plastic. In a specific implementation, the number of fiber optic cables equals the number of openings on bottom surface 1211. For example, if there are two openings on the bottom surface, then there will be two fiber optic cables. If there are three openings on the bottom surface, then there will be three fiber optic cables. If there are four openings on the bottom surface, then there will be four fiber optic cables, and so forth. Each opening on the bottom surface may then include an end of a fiber optic cable.

In another embodiment, the number of fiber optic cables may not equal the number of openings on the bottom surface. The number of fiber optic cables may exceed the number of openings on the bottom surface. For example, the bottom surface may include one or more openings that each includes two, three, four, five, six, seven, or more than seven ends fiber optic cable.

The tip has a thickness as shown by a distance y44. In a specific implementation, the thickness is about 2 millimeters. However, the thickness may range from about 1.5 millimeters to about 5 millimeters. For example, the thickness (i.e., y44) may be about 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 4.1, 4.2, 4.3, 4.4, 4.5, 4.6, 4.7, 4.8, 4.9, 5, or more than 5 millimeters. In some embodiments, the thickness will be less than 1.5 millimeters.

Generally, a smaller thickness (or thinner profile) is desirable to allow, for example, a smaller incision to be made. A smaller incision allows for faster healing and less scarring. Patients may also experience fewer infections. The thickness is typically a function of the distance the blade protrudes away from the bottom surface of the tip, the number of fiber optic cables in the tip, and the diameter (or cross sectional area) of the fiber optic cables in the tip. A large diameter nerve as compared to a small diameter nerve may require a taller blade in order to properly retract the nerve. This may then result in a thicker tip. A large diameter nerve may also require additional fiber optic cable and larger diameter fiber optic cable as compared to a small diameter nerve in order to properly transmit the light into the nerve and receive the light from the nerve.

The blade protrudes at a distance y45 away from the bottom surface of the tip. In a specific implementation, y45 is about 2.8 millimeters. However, it can range from about 2 millimeters to about 4 millimeters, including less than 2 millimeters and more than 4 millimeters. For example, distance y45 may be about 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, or more than 4 millimeters. Generally, distance y45 varies proportionally to the size of the nerve being retracted. For example, a large nerve may require a large distance y45 as compared to a small nerve.

In a specific implementation, a side profile of this tip shows a back portion 1225 of the tip tapering (1220) to meet the blade at a point 1217. In some embodiments, the profile may include an ogee curve. This tapered profile helps to avoid contact injury to the nerve and other structures surrounding the nerve. The tapered profile helps to minimize the displacement of other structures surrounding the nerve. Also, tapering the profile results in a smaller profile which occupies less space at the surgical site and thus provides additional room for the surgeon to work in.

Figure 13:
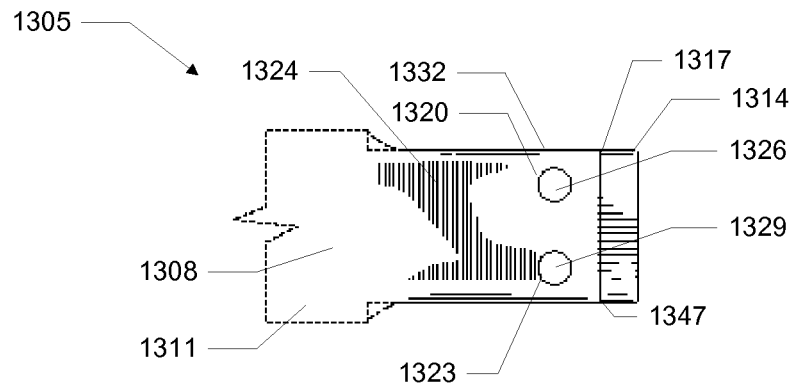
FIG. 13 shows a bottom view of the first embodiment of a tip.

FIG. 13 shows a bottom view of the first embodiment of a tip 1305. The tip is coupled to a distal end 1308 of a shaft 1311. A retractor portion 1314 is coupled at a distal end 1317 of the tip which is opposite distal end 1308. In this example, the tip includes an opening 1320 and an opening 1323 on a bottom surface 1324 of the tip. Opening 1320 includes a source structure 1326. Opening 1323 includes a detector structure 1329.

Although this example shows two openings (i.e., 1320 and 1323), other embodiments may have more or less than two openings. There may be one, two, three, four, five, six, seven, eight, or more than eight openings. A specific embodiment may not have any openings on the bottom surface. For example, the tip or a portion of the tip may be constructed of a light-transparent material, such as clear plastic. Light from source structure 1326 could then pass through the light-transparent material, into the tissue, and then be received by detector structure 1329 as the light passes back through the light-transparent material. As another example, the source structure, detector structure, or both may be located outside a perimeter 1332 of the bottom surface.

Figure 14:
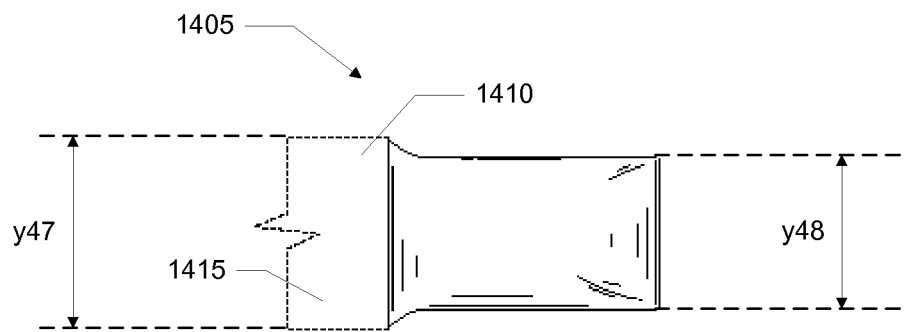
FIG. 14 shows a top view of the first embodiment of a tip coupled to the shaft of a tissue retractor oximeter.

FIG. 14 shows a top view of the first embodiment of a tip 1405 coupled to a distal end 1410 of a shaft 1415. A width y47 of the shaft may be greater than a width y48 of the tip.

In a specific embodiment, the width of the shaft is about 24 percent greater than the width of the tip. For example, in an implementation, the width of the tip may be 2.5 millimeters. The width of the shaft may then be 3.1 millimeters (i.e., 2.5 millimeters*1.24=3.1 millimeters).

In another embodiment, the width of the shaft is about 29 percent greater than the width of the tip. For example, if the width of the tip is about 4 millimeters then the width of the shaft will be about 5.2 millimeters (i.e., 4 millimeters*1.29=5.2 millimeters).

As another example, if the width of the tip is about 8 millimeters then the width of the shaft will be about 10.3 millimeters. The width of the shaft may vary from about 20 percent to about 35 percent greater than the width of the tip. However, in other implementations, the width of the shaft may be less than 25 percent greater than the width of the tip or more than 35 percent greater than the width of the tip. Furthermore, an implementation may include a shaft having a width that is less than the width of the tip.

Figure 15:
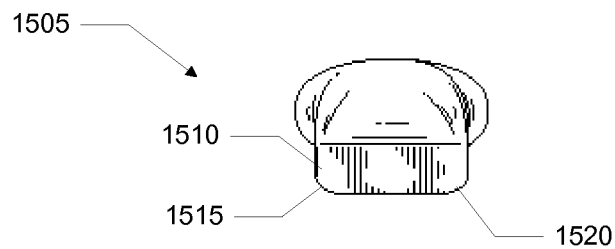
FIG. 15 shows a front view of the first embodiment of a tip.

FIG. 15 shows a front view of the first embodiment of a tip 1505 including a retractor portion 1510. In a specific embodiment, the retractor portion includes any number of curved and straight line segments. For example, in FIG. 15, the retractor portion has the shape of a rectangle with curved edges such as corners 1515 and 1520. The curved or rounded or blunted edges help to avoid contact injury to the nerve and other structures surrounding the nerve.

Figure 16:
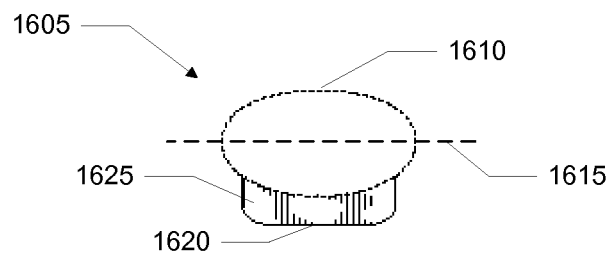
FIG. 16 shows a back view of the first embodiment of a tip.

FIG. 16 shows a back view of the first embodiment of a tip 1605 with an outline of a shaft 1610 shown as a dotted line. In a specific embodiment, a cross-section of the shaft has the shape of an ellipse. A major axis 1615 of the elliptically-shaped shaft may be parallel to a longitudinal edge 1620 of a retractor portion 1625. However, it should be appreciated that the cross-section may have any shape. The shape may be composed of straight line segments such as a polygon (e.g., square, rectangle, triangle, and parallelogram), composed of curved line segments (e.g., oval, ellipse, crescent, and circle), or combinations of these (e.g., semicircle).

One advantage of this particular orientation is that it allows the user to comfortably grip and hold the tool. That is, the user can grip the sides of the tool using their thumb and middle finger. The user's index finger can then rest or apply downward pressure on the larger side (i.e., major axis) of the elliptical shape.

Figure 17:
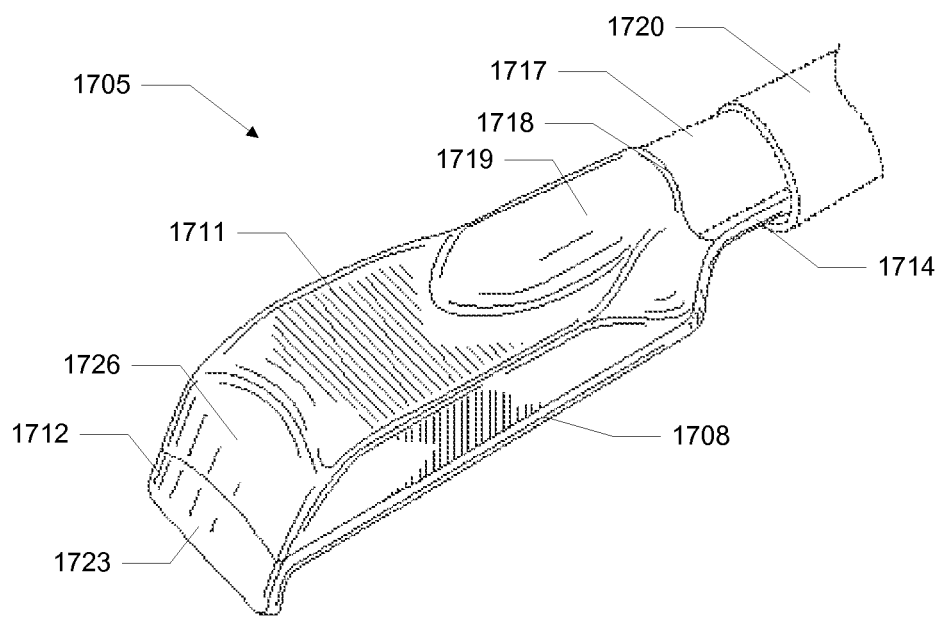
FIG. 17 shows a perspective view of a second embodiment of a tip.

FIG. 17 shows a perspective view of a second embodiment of a tip 1705. The tip includes a bottom surface 1708 (or tissue-facing surface). Optical fibers may be encased or sealed in an encasement 1711. The tip includes a blade or retractor portion 1712. The tip is attached to a shaft 1714. A cable 1717 is connected to the encasement. A jacket 1720 encloses the cable and shaft. In this second embodiment, the tip has a width of about 5 millimeters.

As discussed above for FIG. 11, the fiber optic cables are encased in or sealed using an epoxy, adhesive, resin, plastic, or similar material or compound. The epoxy (or other material) holds the fibers in place, prevents damage to the fibers, and prevents detaching of the fibers from the sensor openings during use. The shape of the epoxy or other material (i.e., encasement 1711) may be sculpted as shown to facilitate ease in use of the device.

In a specific embodiment, the retractor portion has a concave surface 1723 which transitions into a concave surface 1726 of the encasement. Furthermore, the concave surfaces are sloped at an obtuse angle relative to bottom surface 1708. These features allow, for example, better visualization of the surgical site than would otherwise be the case if the encasement, retractor portion, or both projected over the surgical site.

The smooth concave surfaces, in addition to the tip's rounded edges and corners, help to avoid contact injury to the nerve and other structures surrounding the nerve.

In the example shown in FIG. 17, cable 1717 is placed along the top surface of the shaft. However, in other embodiments, the cable may instead run along the bottom surface of the shaft. The cable enters a lateral edge 1718 of the encasement and then travels along a portion of the top surface of the encasement as shown by bulge 1719.

In other embodiments, however, the cable may not enter at the lateral edge of the encasement. For example, the cable may enter through the top surface of the encasement, at a longitudinal edge of the encasement, or combinations of these, i.e., there may be more than one cable.

The cable is wrapped by jacket 1720. The jacket helps to secure the cable to the shaft. However, in another embodiment, the cable may be secured using a different system. For example, the cable may be secured to the shaft using an adhesive, using one or more bands wrapped around the cable and the shaft, wrapping the cable around the shaft, and the like.

In a specific embodiment, the jacket does not extend all the way to the encasement. In other embodiments, the jacket may extend all the way to the encasement. In still other embodiments, the jacket may extend to cover the encasement.

Figure 18:
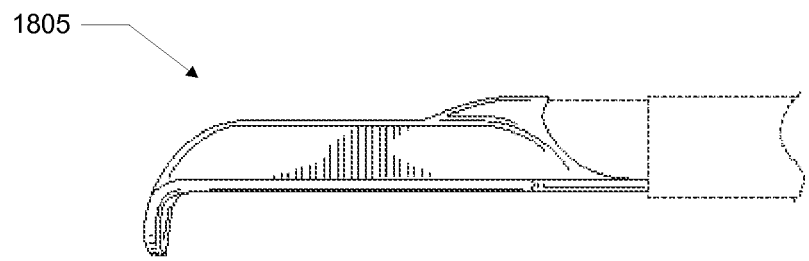
FIG. 18 shows a left-hand side view of the second embodiment of a tip.

FIG. 18 shows a left-hand side view of the second embodiment of a tip 1805.

Figure 19:
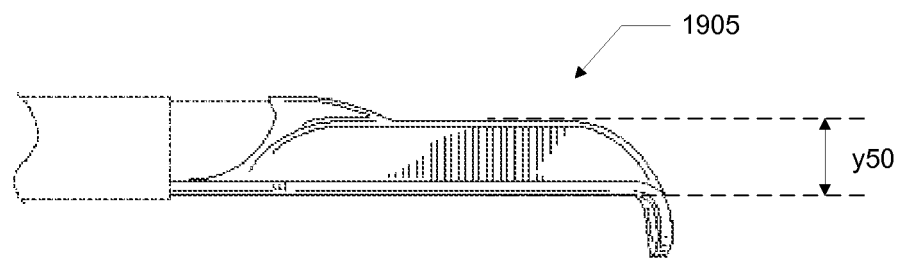
FIG. 19 shows a right-hand side view of the second embodiment of a tip.

FIG. 19 shows a right-hand side view of the second embodiment of a tip 1905. In a specific embodiment, the tip has a thickness y50 of about 3 millimeters, but may range from about 2.5 millimeters to about 3.5 millimeters.

Figure 20:
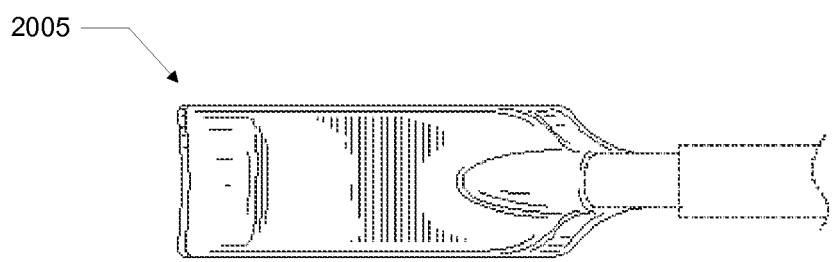
FIG. 20 shows a top view of the second embodiment of a tip.

FIG. 20 shows a top view of the second embodiment of a tip 2005.

Figure 21:
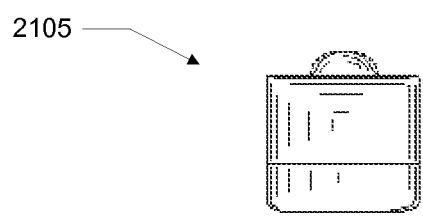
FIG. 21 shows a front view of the second embodiment of a tip.

FIG. 21 shows a front view of the second embodiment of a tip 2105.

Figure 22:
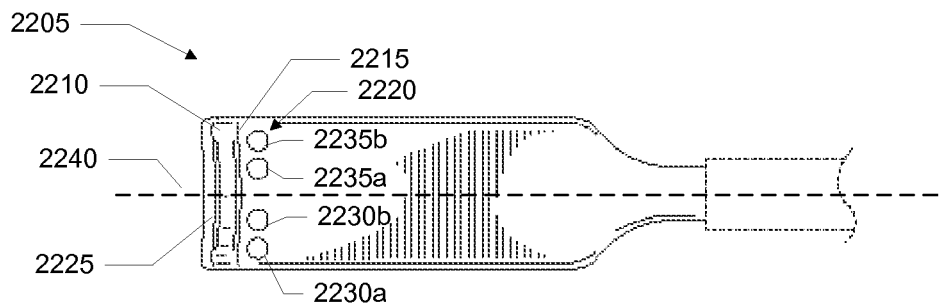
FIG. 22 shows a geometric sensor arrangement with four sensors having a spacing relative to a y-axis.

FIG. 22 shows a bottom view of the second embodiment of a tip 2205. In this example, a retractor portion 2210 has an edge profile having a slight arc or crescent. A convex side 2215 of the arc is positioned near a linear source-detector array 2220. A concave side 2225 of the arc is opposite the convex side.

One advantage of the convex side of the retractor portion is a more uniform distribution of stresses across the length of the nerve as it is being retracted. That is, as the nerve is being retracted, then there will be less pinching (i.e., high pressure points or relatively higher force per unit area) at the outermost points of the arc or crescent. An arc shape generally reduces the number of high stress points when retracting a nerve. However, in other implementations, other edge profiles and shapes may be used including having the concave side of the arc positioned on the side of the source-detector array.

In the example shown in FIG. 22, the source-detector array is approximately tangent to convex side 2215. That is, the source-detector array is arranged on a line as opposed to a curve. In this embodiment, a distance from a source structure, detector structure, or both to convex side 2215 may vary. For example, a first distance from source structure 2230*a* to the convex side is different from a second distance from source structure 2230*b* to the convex side. In a specific implementation, the first distance is greater than the second distance. However, in another implementation the first distance may be less than the second distance. This may be the case, for example, when the concave side of the retractor portion is positioned on the side of the source-detector array. It may also be the case when the source structures, detector structures, or both are in an offset arrangement, i.e., not all of the source and detector structures are arranged on the same line.

Furthermore, in a symmetrical source-detector arrangement, one side (e.g., top half) is a mirror image of another side (e.g., bottom half). For example, in FIG. 22 an axis 2240 running longitudinally through the shaft divides the bottom surface into a top half and bottom half. The top half and bottom half are mirror images of each other. A third distance from detector structure 2235*a* to the convex side is equal to the second distance (i.e., source structure 2230*b* to the convex side). Likewise, a fourth distance from detector structure 2235*b* is equal to the first distance (i.e., source structure 2230*a* to the convex side).

The radius of the crescent-shaped retractor portion may be constant, as shown in FIG. 22, or it may be increasing or decreasing. For example, in a specific implementation, the radius increases from source structure 2230*a* to detector structure 2235*b*. Thus, a first distance from source structure 2230*a* to the convex side will be greater than a second distance from source structure 2230*b* to the convex side. The second distance will be greater than a third distance from detector structure 2235*a* to the convex side. The third distance will be greater than a fourth distance from detector structure 2235*b* to the convex side.

As another example, the radius may be decreasing from source structure 2230*a* to detector structure 2235*b*. Thus, a first distance from source structure 2230*a* to the convex side will be less than a second distance from source structure 2230*b* to the convex side. The second distance will be less than a third distance from detector structure 2235*a* to the convex side. The third distance will be less than a fourth distance from detector structure 2235*b* to the convex side.

In another embodiment, the source-detector array may be arranged on a curve. The curve may match the curve of the convex side of the retractor portion. Thus, a first distance from source structure 2230*a* to the convex side will equal a second distance from source structure 2230*b* to the convex side. A third distance from detector structure 2235*a* to the convex side will equal a fourth distance from detector structure 2235*b* to the convex side.

FIG. 22 also shows another example of a geometric arrangement of source structures 2230*a* and 2230*b* and detector structures 2235*a* and 2235*b*. In this first geometric arrangement, a first distance between a first source structure (i.e., 2230*a*) and a second source structure (i.e., 2230*b*) is different from a second distance between the second source structure (i.e., 2230*b*) and a first detector structure (i.e., 2235*a*). The second distance may be larger than the first distance. Furthermore, a third distance between a second detector structure (i.e., 2235*b*) and the first detector structure may be equal to the first distance.

However, many other different geometric arrangements are possible. For example, in a second geometric arrangement, the first, second, and third distances are equal. In a third geometric arrangement, the second distance is less than the first distance, third distance, or both. The first and third distances are equal. In a fourth geometric arrangement, the third distance is greater than the first distance, second distance, or both. The first and second distances are equal. In a fifth geometric arrangement, the first distance is greater than the second distance, third distance, or both. The second and third distances are equal.

FIG. 22 shows various geometric arrangements of source and detector structures relative to a single axis where the source and detector structures were all arranged on a line. However, other geometric arrangements may instead or additionally have distances between source and detector arrangements relative to a second axis.

Figure 23:
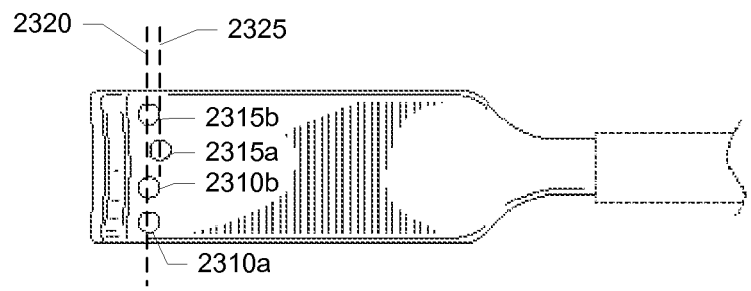
FIG. 23 shows a geometric sensor arrangement with four sensors having a spacing relative to an x-axis.

For example, FIG. 23 shows another example of a geometric arrangement having distances relative to an x-axis. This specific example includes four sensors including source structures 2310*a* and 2310*b* and detector structures 2315*a* and 2315*b*. A first distance is between a first source structure (i.e., 2310*a*) and a second source structure (i.e., 2310*b*). A second distance is between the second source structure and a first detector structure (i.e., 2315*b*). A third distance is between the first detector structure and a second detector structure (i.e., 2315*b*).

In a first geometric arrangement shown in FIG. 23, a first axis 2320 passes through the reference point of the first and second source structures and second detector structure. A second axis 2325 passes through the reference point of the first detector structure. The first axis is parallel to the second axis, but offset to the left of the second axis, i.e., the first and second axes are not coincident. In this first geometric arrangement, the third distance is equal to the second distance. The first distance is less than the third or second distance.

However, many other different geometric arrangements are possible. For example, in a second geometric arrangement, a first axis passes through the reference point of the first and second source structures and first detector structure. A second axis passes through the reference point of the second detector structure. The first axis is parallel to the second axis, but offset to the left side of the second axis, i.e., the first and second axes are not coincident. In this second geometric arrangement, the first and second distances are equal. The third distance is greater than the first or second distances.

In a third geometric arrangement, a first axis passes through the reference point of the second source structure and first and second detector structures. A second axis passes through the reference point of the first source structure. The first axis is parallel to the second axis, but offset to the left side of the second axis, i.e., the first and second axes are not coincident. In this third geometric arrangement, the first distance is greater than the second distance, third distance, or both. The second distance is equal to the third distance.

In a fourth geometric arrangement, a first axis passes through the reference point of the first and second detector structures and the first source structure. A second axis passes through the reference point of the second source structure. The first axis is parallel to the second axis, but offset to the left side of the second axis, i.e., the first and second axes are not coincident. In this fourth geometric arrangement, the third distance is less than the first distance, second distance, or both. The first distance is equal to the second distance.

In a fifth geometric arrangement, a first axis passes through the reference point of the first and second source structures. A second axis passes through the reference point of the first and second detector structures. The first axis is parallel to the second axis, but offset to the left side of the second axis, i.e., the first and second axes are not coincident. In this fifth geometric arrangement, the second distance is greater than the first distance, the third distance, or both. The first distance equals the third distance.

In a sixth geometric arrangement, a first axis passes through the reference point of the first and second detector structures. A second axis passes through the reference point of the first and second source structures. The first axis is parallel to the second axis, but offset to the left side of the second axis, i.e., the first and second axes are not coincident. In this sixth geometric arrangement, the second distance is greater than the first distance, the third distance, or both. The first distance equals the third distance.

In a seventh geometric arrangement, a first axis passes through the reference point of the second source structure and second detector structure. A second axis passes through the reference point of the first source structure and first detector structure. The first axis is parallel to the second axis, but offset to the left side of the second axis, i.e., the first and second axes are not coincident. In this seventh geometric arrangement, the first, second, and third distances are equal.

In an eighth geometric arrangement, a first axis passes through the reference point of the first source structure and first detector structure. A second axis passes through the reference point of the second source structure and second detector structure. The first axis is parallel to the second axis, but offset to the left side of the second axis, i.e., the first and second axes are not coincident. In this eighth geometric arrangement, the first, second, and third distances are equal.

In a ninth geometric arrangement, a first axis passes through the reference point of the first source structure and second detector structure. A second axis passes through the reference point of the second source structure and first detector structure. The first axis is parallel to the second axis, but offset to the left side of the second axis, i.e., the first and second axes are not coincident. In this ninth geometric arrangement, the second distance is less than the first distance, third distance, or both. The first distance is equal to the third distance.

In a tenth geometric arrangement, a first axis passes through the reference point of the second source structure and first detector structure. A second axis passes through the reference point of the first source structure and second detector structure. The first axis is parallel to the second axis, but offset to the left side of the second axis, i.e., the first and second axes are not coincident. In this tenth geometric arrangement, the second distance is less than the first distance, third distance, or both. The first distance is equal to the third distance.

Figure 24:
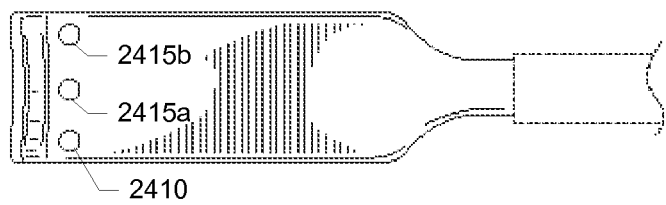
FIG. 24 shows a geometric sensor arrangement with three sensors having a spacing relative to a y-axis.

FIG. 23 shows various source and detector geometric arrangements with respect to the tip having four openings. However, similar geometric arrangements may be had for tips with more than four or less than four openings. FIG. 24 shows a source and detector geometric arrangement where the tip includes three openings. This specific example includes a source structure 2410 and detector structures 2415a and 2415b. A first distance is between the source structure and a first detector structure (i.e., 2415a). A second distance is between the first detector structure and a second detector structure (i.e., 2415b). The source and detector structures may be arranged on a line. In this first geometric arrangement, the first and second distances are equal.

However, many other different geometric arrangements are possible. For example, in a second geometric arrangement, the first distance is less than the second distance.

In a third geometric arrangement, the first distance is greater than the second distance.

FIG. 24 shows various geometric arrangements of source and detector structures relative to a single axis where the source and detector structures are arranged on the same line. However, other geometric arrangements may instead or additionally have distances between source and detector arrangements relative to a second axis.

Figure 25:
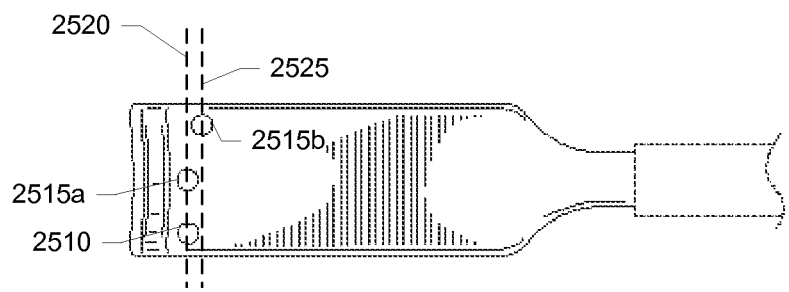
FIG. 25 shows a geometric sensor arrangement with three sensors having a spacing relative to an x-axis.

For example, FIG. 25 shows another example of a geometric arrangement having distances relative to an x-axis. This specific example includes three sensors including a source structure 2510 and detector structures 2515a and 2515b. A first distance is between the source structure and a first detector structure (i.e., 2515a). A second distance is between the first detector structure and a second detector structure (i.e., 2515b).

In a first geometric arrangement shown in FIG. 25, a first axis 2520 passes through the reference point of source structure and first detector structure. A second axis 2525 passes through the reference point of the second detector structure. The first axis is parallel to the second axis, but offset to the left side of the second axis, i.e., the first and second axes are not coincident. In this first geometric arrangement, the first distance is less than the second distance.

However, many other different geometric arrangements are possible. For example, in a second geometric arrangement, a first axis passes through the reference point of the first and second detector structures. A second axis passes through the reference point of the source structure. The first axis is parallel to the second axis, but offset to the left side of the second axis, i.e., the first and second axes are not coincident. In this second geometric arrangement, the first distance is greater than the second distance.

In a third geometric arrangement, a first axis passes through the reference point of the first source structure and second detector structure. A second axis passes through the reference point of the first detector structure. The first axis is parallel to the second axis, but offset to the left side of the second axis, i.e., the first and second axes are not coincident. In this third geometric arrangement, the first distance is equal to the second distance.

In a fourth geometric arrangement, a first axis passes through the reference point of the first detector structure. A second axis passes through the reference point of the first source structure and second detector structure. The first axis is parallel to the second axis, but offset to the left side of the second axis, i.e., the first and second axes are not coincident. In this fourth geometric arrangement, the first distance is equal to the second distance.

Figure 26:
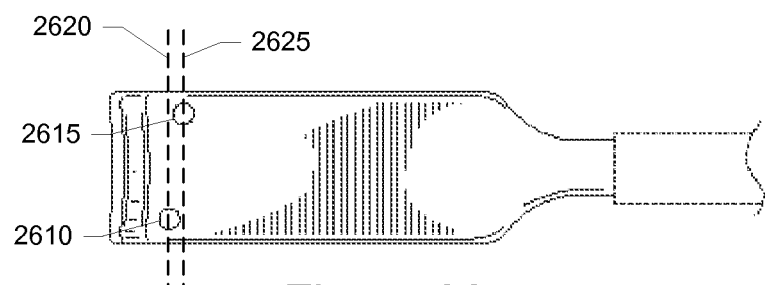
FIG. 26 shows a geometric sensor arrangement with two sensors having a spacing relative to an x-axis.

FIG. 25 shows various source-detector geometric arrangements with respect to the tip having three openings. However, similar geometric arrangements may be had for tips with less than three openings, such as two openings. FIG. 26 shows a source and detector geometric arrangement where the tip includes two openings. This specific example includes a source structure 2610 and a detector structure 2615. A first axis 2620 passes through the reference point of the source structure. A second axis 2625 passes through the reference point of the detector structure. The first axis is parallel to the second axis, but offset to the left side of the second axis, i.e., the first and second axes are not coincident.

In another embodiment, a first axis passes instead through the reference point of the detector structure and the second axis passes through the reference point of the source structure. The first axis is parallel to the second axis, but offset to the left side of the second axis, i.e., the first and second axes are not coincident.

Figure 27:
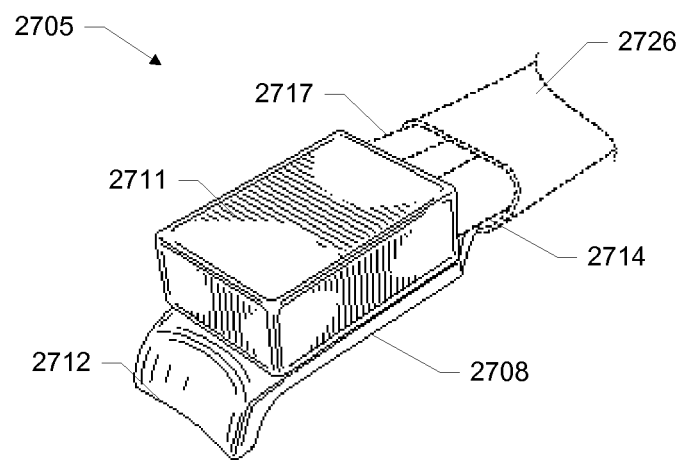
FIG. 27 shows a perspective view of a third embodiment of a tip.

FIG. 27 shows a perspective view of a third embodiment of a tip 2705. The tip includes a back surface 2708 onto which a sensor unit 2711 has been attached. The tip further includes a retractor portion or blade 2712. The tip is attached to a shaft 2714. Fiber optic cables are encased in an inner jacket 2717 and are connected to the sensor unit. An outer jacket 2726 encloses the inner jacket and shaft. In this third embodiment, the tip has a width of about 5 millimeters.

The sensor unit may be attached to the back surface using any method such as an adhesive (e.g., epoxy, glue), snap-fit, screws, or magnets. The sensor unit may instead or additionally be secured by wrapping the sensor unit to the retractor with tape, heat-shrink tubing, and the like.

The tip shown in FIG. 27 is slightly thicker than the tip shown in other embodiments, such as FIG. 18. Both embodiments have advantages. For example, a thicker tip may provide additional room for additional or thicker fiber optic cables. This may result in more accurate measurements. A thinner tip may be inserted into a smaller incision as opposed to a thicker tip.

Figure 28:
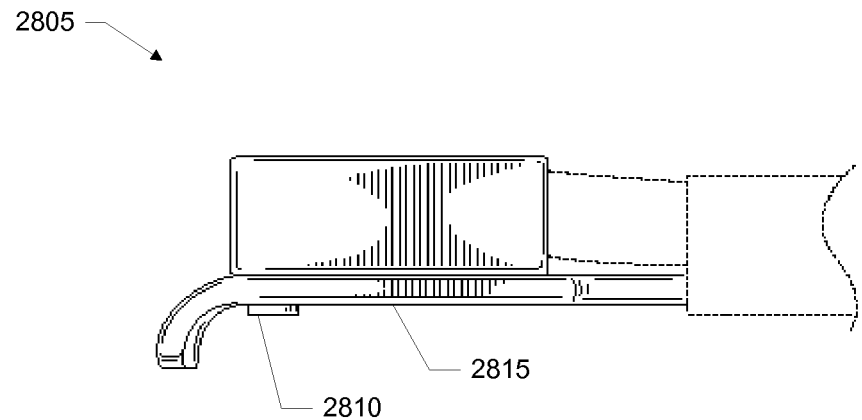
FIG. 28 shows a left-hand side view of the third embodiment of a tip.

FIG. 28 shows a left-hand side view of the third embodiment of a tip 2805. The tip includes a sensor structure 2810 which protrudes past a bottom surface 2815. The distance that the sensor structure protrudes past the bottom surface varies from about 0.1 millimeter to about 1 millimeter. For example, the sensor may protrude past the bottom surface by about 0.1, 0.2, 0.3, 0.4, 0.5, 0.6, 0.7, 0.8, 0.9, 1.0, or more than 1.0 millimeters. In other implementations, the sensor structure may protrude less than 0.1 millimeters past the bottom surface.

Locating the sensor structure past the bottom surface helps to ensure, for example, that the sensor structure contacts the tissue to be measured. The sensor structure may include one or more source and detector structures. In a specific implementation, all sensors (i.e., the source and detectors) will protrude past the bottom surface by the same amount. In another implementation, the sensors may protrude past the bottom surface by varying amounts.

Figure 29:
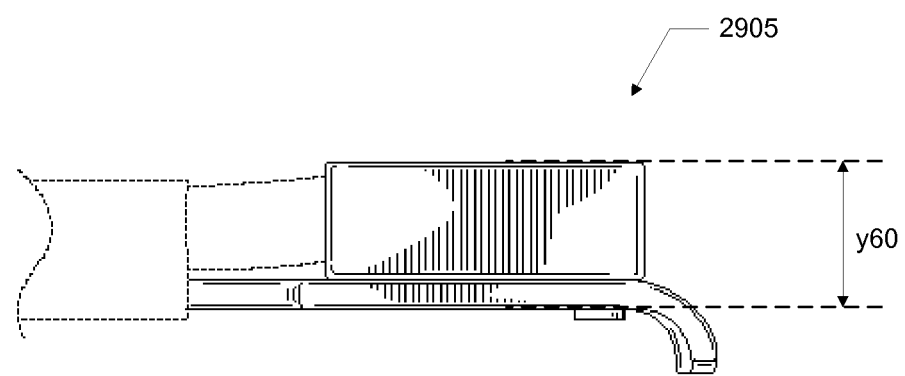
FIG. 29 shows a right-hand side view of the third embodiment of a tip.

FIG. 29 shows a right-hand side view of the third embodiment of a tip 2905. In a specific embodiment, the tip has a thickness y60 of about 5 millimeters, but may range from about 3 millimeters to about 8 millimeters.

Figure 30:
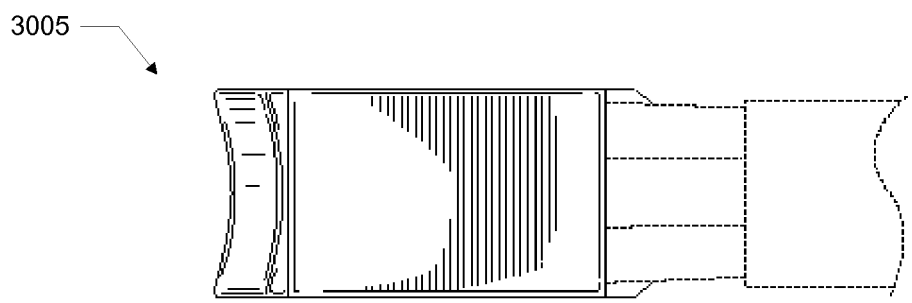
FIG. 30 shows a top view of the third embodiment of a tip.

FIG. 30 shows a top view of the third embodiment of a tip 3005.

Figure 31:
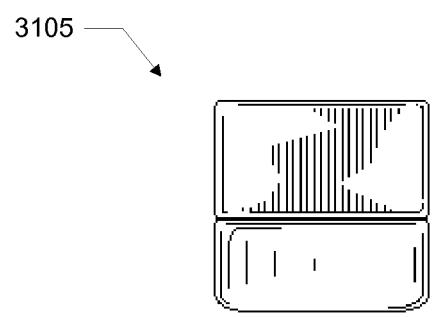
FIG. 31 shows a front view of the third embodiment of a tip.

FIG. 31 shows a front view of the third embodiment of a tip 3105.

Figure 32:
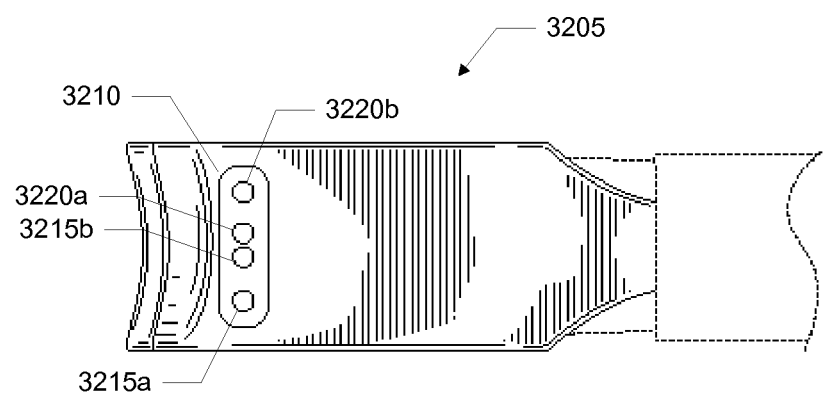
FIG. 32 shows a bottom view of the third embodiment of a tip.

FIG. 32 shows a bottom view of the third embodiment of a tip 3205. The tip includes a slot 3210. Within the slot, there are four sensor openings. In an implementation, these sensor opening are ends of fiber optic cables. Further, these openings are for source structures 3215a and 3215b and detector structures 3220a and 3220b.

In a specific implementation, the slot has the shape of an obround (i.e., a shape with two parallel sides and semicircular ends). However, the slot may be of any shape. The shape may be composed of straight line segments such as a polygon (e.g., square, rectangle, triangle, and parallelogram), composed of curved line segments (e.g., oval, ellipse, crescent, and circle), or combinations of these (e.g., semicircle and obround).

In the example shown in FIG. 32, the slot includes openings for four ends of fiber optic cable. A first end of fiber optic cable is coupled to source structure 3215a. A second end of fiber optic cable is coupled to source structure 3215b. A third end of fiber optic cable is coupled to detector structure 3220a. A fourth end of fiber optic cable is coupled to detector structure 3220b.

However, in various implementations, an slot may include less than four ends of fiber optic cable or more than four ends of fiber optic cable. For example, a slot may include one, two, three, four, five, six, or more than six ends of fiber optic cable. Additional fiber optic cable allows, for example, additional data points to be taken.

In implementations discussed so far in this application, each opening of the probe has a single fiber associated with it. However, in further implementations of the invention, each opening of the probe may have multiple fibers-two or more- associated with it. Or, each opening of the probe may have multiple light paths or light channels associated with it.

These light paths can be used simultaneously for transmitting to tissue or receiving light from tissue. Within a single opening, there may be two source structures, two detector structures, or one source and one detector structure. And for a single probe or retractor, there may be two or more such openings with multiple light channels.

Figure 33:
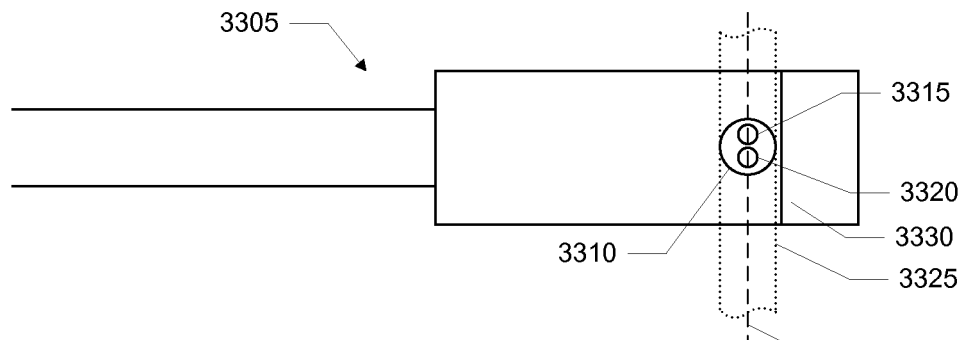
FIG. 33 shows a bottom view of a tip with a single opening having source and detector structures in a first geometric arrangement.

By way of example, FIG. 33 shows a tip 3305 with a single opening 3310. The single opening includes a source structure 3315 and a detector structure 3320, each of which includes an end of a single optical fiber. Although opening 3310 is shown as a circle, this opening can have any shape, including obround, oblong, oval, or other shapes as discussed elsewhere in this application.

A tissue (i.e., nerve) 3325 is shown being pulled back via a retractor portion 3330. A plane 3335 passes through the reference point of the source and detector structures.

In a specific embodiment, the source and detector structures are aligned in the single opening such that plane 3335 is approximately parallel to a longitudinal axis of the nerve. This helps to ensure, for example, that light passing through the source structure will be transmitted into the nerve and that the light from the nerve will be received by the detector structure.

The source and detector structures may be separated by any distance. For example, in a specific embodiment, the source and detector structures are separated by a distance of about 1.5 millimeters. In another embodiment, the source and detector structures are separated by a distance of about 5 millimeters. Thus, the separation will typically range from about 1.5 millimeters to about 5 millimeters. However, in other implementations, the separation is less than 1.5 millimeters. For example, the source and detector structures may touch each other. In other implementations, the separation is greater than 5 millimeters.

Generally, a smaller separation may result in a smaller tip which in turn results in a smaller incision. A larger separation may result in the light from the source structure penetrating deeper into the tissue before the light is received by the detector structure.

Figure 34:
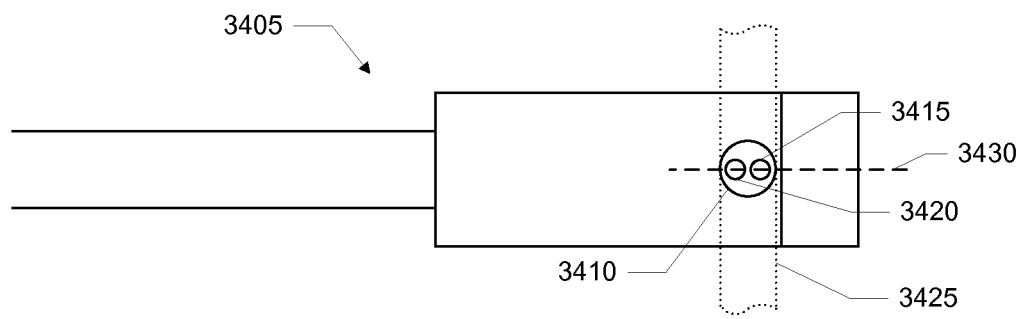
FIG. 34 shows a bottom view of a tip with a single opening having source and detector structures in a second geometric arrangement.

FIG. 34 shows another implementation of a probe with a single opening having multiple fibers. This implementation is similar to that described in FIG. 33, but the orientation of the fiber is perpendicular to the orientation in FIG. 33.

Specifically, FIG. 34 shows a tip 3405 with a single sensor opening 3410 that includes source and detector structures 3415 and 3420, respectively. In this example, the source and detector structures are arranged orthogonal to a nerve 3425. That is, a plane 3430 that passes through the reference point of the source and detector structures is at a 90-degree angle relative to a longitudinal axis of the nerve.

Figure 35:
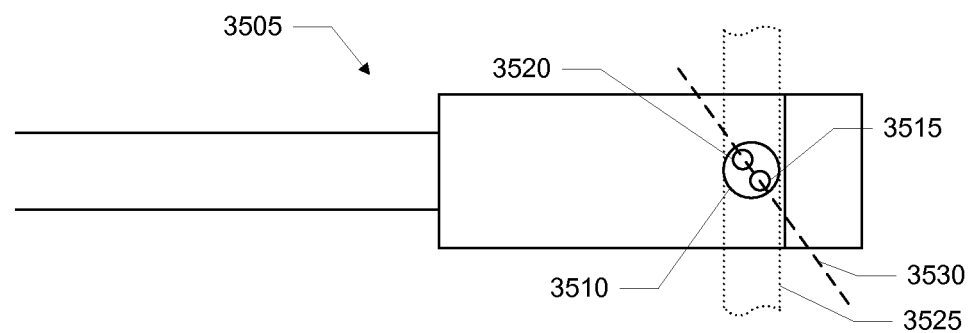
FIG. 35 shows a bottom view of a tip with a single opening having source and detector structures in a third geometric arrangement.

FIG. 35 shows another implementation of a probe with a single sensor opening having multiple fibers. This implementation is similar to that described in FIG. 33, but the orientation of the fiber is at an angle compared to the orientation in FIG. 33. This angle may be any angle relative to the orientation of fibers if FIG. 33.

It should be appreciated, however, that the source and detector structures may have any arrangement. Specifically, FIG. 35 shows a tip 3505 with a single opening 3510 that includes source and detector structures 3515 and 3520, respectively. In this example, the source and detector structures are arranged at an angle to a nerve 3525. That is, a plane 3530 that passes through the reference point the source and detector structures is at some angle relative to a longitudinal axis of the nerve. The angle may be any angle. For example, the angle may be 0 degrees as shown in FIG. 33, 90 degrees as shown in FIG. 34, or any other angle as shown in FIG. 35.

Figure 36:
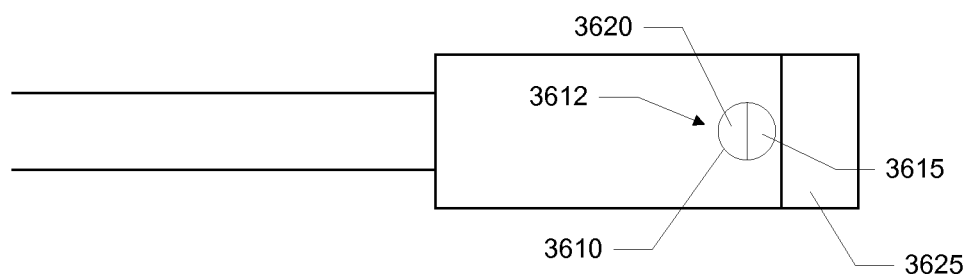
FIG. 36 shows a bottom view of a tip with a single opening having a first embodiment of a fiber with multiple light channels.

FIG. 36 shows another implementation of a probe with a single sensor opening 3610 having a fiber with multiple light paths. This fiber may be referred to as a split channel fiber. There is a single circular fiber 3612 with two semicircular light channels 3615 and 3620.

In a specific implementation, light channel 3615 is a source channel and light channel 3620 is a detector channel. For example, light channel 3615 may be used to transmit light into the tissue and light channel 3620 may be used to receive light from the tissue. In another implementation, light channel 3615 is instead the detector channel and light channel 3620 is the source channel.

Although light channels 3615 and 3620 are shown as having semicircular cross sections, these light channels can have any shape. Some examples of the various shapes that they may have include polygons (e.g., square, rectangle, triangle, and parallelogram), shapes with curved line segments (e.g., oval, ellipse, and crescent), or combinations of these.

In a specific implementation as shown in FIG. 36, the light channels are symmetrical. However, in other implementations, the light channels may not be symmetrical. For example, light channel 3615 may have the shape of a square while light channel 3620 has the shape of a semicircle.

Although light channels 3615 and 3620 are shown as having the same cross-sectional areas, this is not always the case. For example, in a specific implementation, light channel 3615 may have a different cross-sectional area than light channel 3620. That is, light channel 3615 may have a greater cross-sectional area than light channel 3620 or light channel 3615 may have a smaller cross-sectional area than light channel 3620.

It should also be appreciated that a single fiber may have more light channels than the two light channels shown in FIG. 36. A single fiber may have any number of light channels.

In a specific implementation, a distance from a first light channel (e.g., 3615) to a blade 3625 is different from a distance from a second light channel (e.g., 3620) to the blade. For example, in FIG. 36, light channel 3615 is closer to the blade than light channel 3620. However, in other implementations, the light channels may be equally spaced from the blade.

Figure 37:
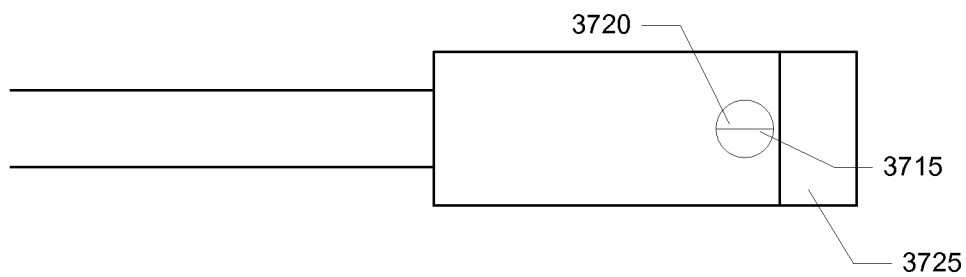
FIG. 37 shows a bottom view of a tip with a single opening having a second embodiment of a fiber with multiple light channels.

The light channels may have any orientation. FIG. 37 shows a different orientation of the light channels where the light channels have been rotated 90 degrees from the configuration shown in FIG. 36. Any other rotation angle may be used. In a specific implementation, as shown in FIG. 37, light channels 3715 and 3720 are equally spaced from a blade 3725.

Figure 38:
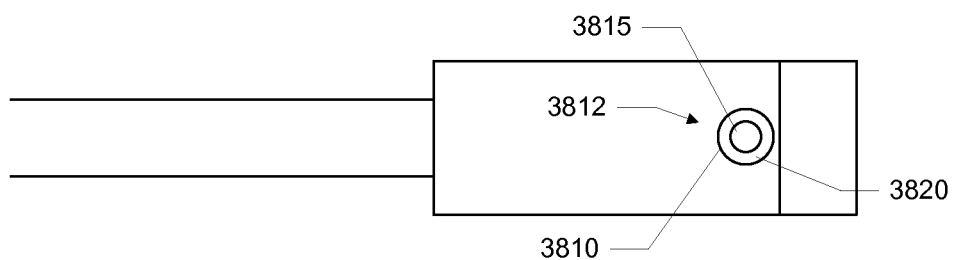
FIG. 38 shows a bottom view of a tip with a single opening having a third embodiment of a fiber with multiple light channels.

FIG. 38 shows another implementation of a probe with a single sensor opening 3810 having a fiber with multiple light channels. There is a concentric core fiber 3812 having an inner core light channel 3815, which is surrounded by an outer core light channel 3820.

In a specific implementation, the inner core light channel is a source channel and the outer core light channel is a detector channel. However, in another implementation, the inner core light channel is a detector channel and the outer core light channel is a source channel.

It should also be appreciated that the inner and outer core light channels may have any shape. Although the inner and outer core light channels are shown as circles, in various other implementations they may be shaped as polygons (e.g., square, rectangle, triangle, and parallelogram), ovals, ellipses, obrounds, or other shapes as discussed elsewhere in this application.

Furthermore, in another implementation, the inner and outer core light channels may not be concentric.

One advantage of the single opening is that additional time and manufacturing is not expended on making multiple openings in the tip. This may result in significant cost savings which in turn may lower the overall cost of the system.

Figure 39:
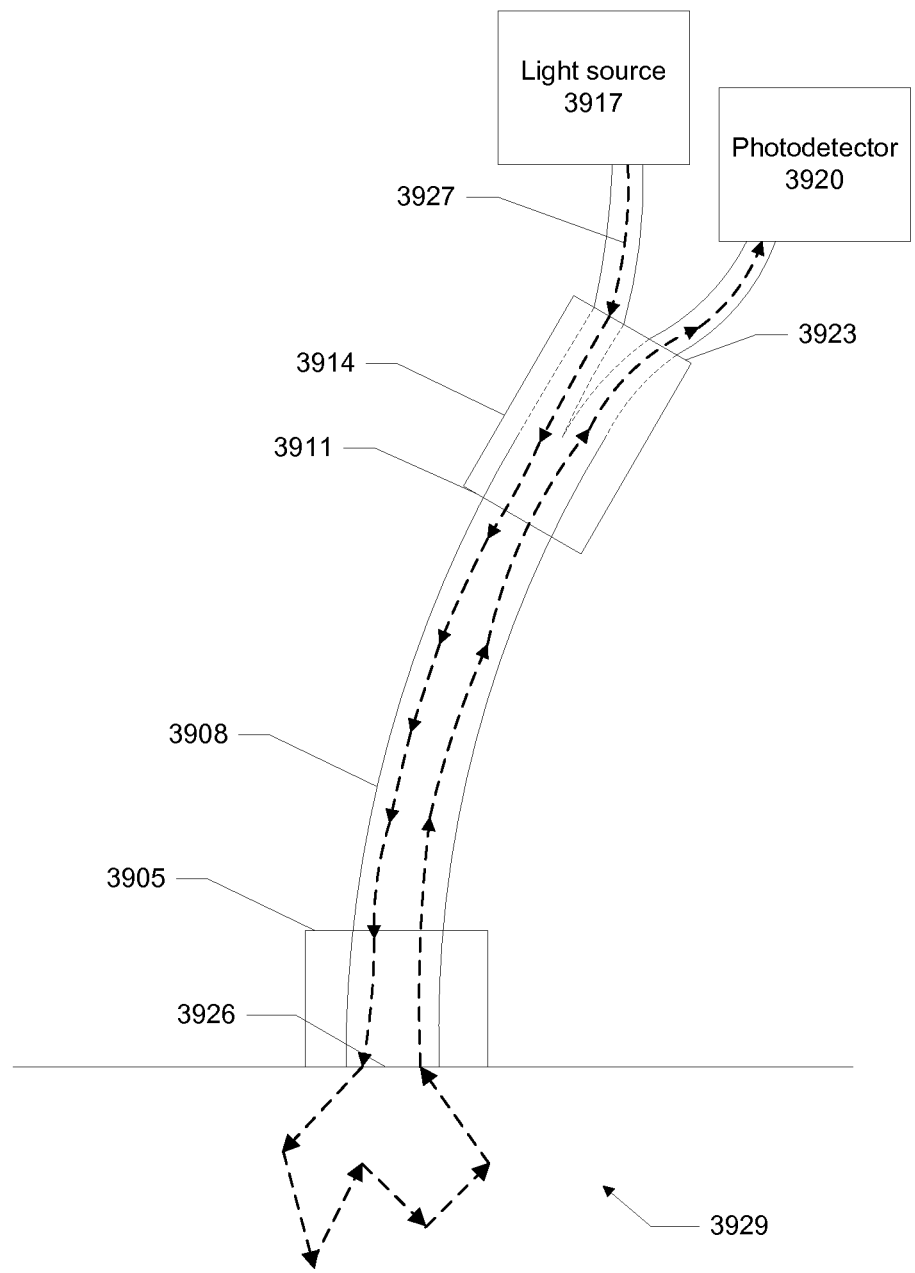
FIG. 39 shows a bottom view of a tip with a single opening having a single optical fiber or single optical fiber bundle in an embodiment of the invention.

FIG. 39 shows a block diagram of an implementation of a sensor using a single optical fiber or single optical fiber bundle and a light combiner. A sensor head 3905 of the sensor is connected to a single fiber 3908, which is connected to a first end 3911 of a light combiner 3914. A source laser diode 3917 and photodiode detector 3920 are connected to a second end 3923 of the light combiner. The sensor head is typically attached to an opening of a probe, such as at an opening 3926 of a retractor.

With this single fiber implementation, the source and detector can share one fiber. This reduces the number of optical fibers needed in implementing a sensor of the invention. Light 3927 is transmitted from light source 3917 through combiner 3914, fiber 3908, and opening 3926 to a tissue 3929 to be measured. Reflected or received light is transmitted from opening 3926, fiber 3908, and combiner 3914 to photodetector 3920. By analyzing the transmitted and received light, a determination of the oxygen saturation can be made.

In an implementation, the source laser diode is capable of outputting two or more different wavelengths of light. This permits the exposing the tissue to different wavelengths of light, such as 690 nanometers and 830 nanometers. Further in an implementation, instead of having one laser diode directly connected to the light combiner, there is another light combiner (not shown) connected in series with the light combiner. This light combiner (not shown) is, in turn, connected to two or more laser diodes, each having a different wavelength. With such a configuration, two or more wavelengths of lights from the different laser diodes can be transmitted to the sensor head through the two light combiners.

In an implementation, there may be any number of sensor openings (e.g., two, three, four, five, or more) in a probe (e.g., retractor) that are connected similarly as shown. This technique of sharing one fiber between a source and a detector reduces the number fibers and sensor openings needed. Previously, there would have been two openings, one for the source and one for the detector. For a probe with two sensor openings and two fibers connected to two light combiners according to a technique as shown in this figure, this would be equivalent to having four sensor openings—two source and two detectors—connected using the previous technique. Reducing the number of openings and fibers generally reduces the cost of the probe, which is especially desirable for making the probe disposable.

In an implementation, the light combiner is located within the monitoring console such as on a circuit board housed by the console. Locating the light combiner within the monitoring console allows, for example, the retractor to be disposed of without having to also dispose of the light combiner.

In an implementation, the light combiner is located external to the monitoring console. For example, the light combiner may be located within the handle of the retractor, along the shaft of the retractor, or within the tip of the retractor.

Further, the implementation in FIG. 39 may be used in combination with the multiple fibers or multiple light paths per single opening discussed above (i.e., see above FIGS. 33-38 and accompanying description). In particular, each light channel can be connected to a light combiner as shown as described.

The openings on the bottom surface of the tip may have any shape. The previous implementations showed circular openings, but other shapes (e.g., square or rectangle) may be used instead. A device may have a combination of openings having different shapes (e.g., a square and a circle).

Figure 40:
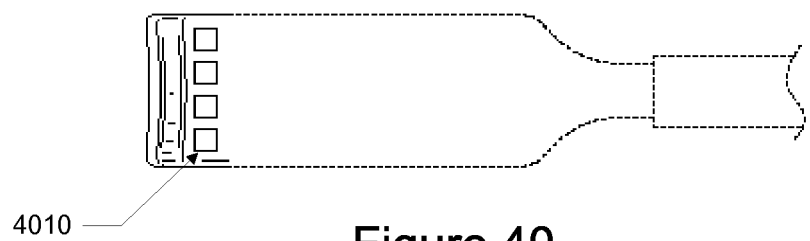
FIG. 40 shows a bottom view of a tip with square openings.
Figure 41:
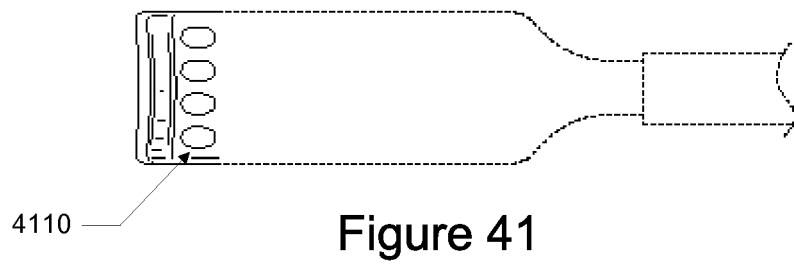
FIG. 41 shows a bottom view of a tip with elliptical openings.
Figure 42:
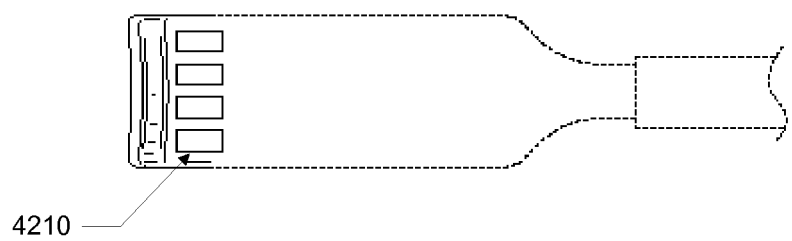
FIG. 42 shows a bottom view of a tip with rectangular openings.

As a further example, FIG. 40 shows a specific implementation of openings 4010 having square shapes. As another example, FIG. 41 shows a specific implementation of openings 4110 having elliptical shapes. In yet another example, FIG. 42 shows a specific implementation of openings 4210 having rectangular shapes. A device can have a combination of openings having different shapes (e.g., squares, ellipses, and rectangles in a single probe).

The optical fibers themselves may have the same cross-sectional shape as the openings on the probe. Or the openings themselves may have a different shape from the cross-sectional shape of the fiber. For example, a square opening can be used to hold a circular fiber. A rectangular opening can hold a circular fiber. A circular opening can hold a rectangular fiber. An oval opening can hold a square fiber. An oval opening can hold two circular fibers. An oval opening can hold a single circular fiber. As can be appreciated, many variations and combinations are possible and only a few examples are provided here.

Furthermore, in other implementations the source and detector openings may have other arrangements besides linear arrangements. For example, FIG. 43 includes source structures 4315a and 4315b and detector structures 4320a and 4320b. The source and detector structures are arranged to form the vertices of a quadrilateral.

There is a first source structure; a second source structure; a first detector structure including optical fiber; and a second detector structure including optical fiber, where the first source structure, second source structure, first detector structure, second detector structure define vertices of a convex quadrilateral, and a first side of the quadrilateral between the first source structure and first detector structure is different in length from a second side of the quadrilateral between the second source structure and the second detector structure.

There is a first source structure; a second source structure; a first detector structure including optical fiber; a second detector structure including optical fiber, where a first distance is between the first source structure and the first detector structure, a second distance is between the first source structure and the second detector structure, a third distance is between the second source structure and the first detector structure, a fourth distance is between the second source structure and the second detector structure. The first distance is not equal to the second, third, and fourth distances, the second distance is not equal to the third and fourth distances, and the third distance is not equal to the fourth.

Figure 43:
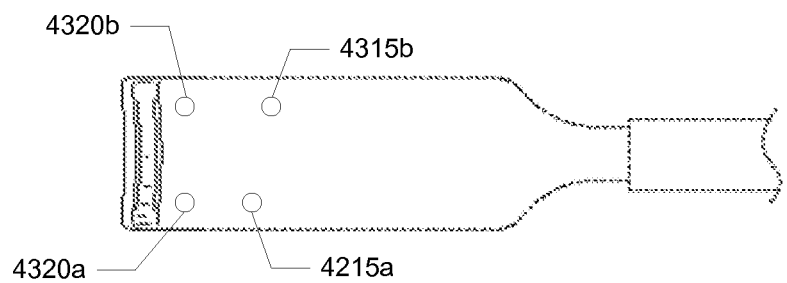
FIG. 43 shows a bottom view of a tip with source and detector openings arranged to form the vertices of a quadrilateral.

In a further implementation of FIG. 43, the openings are arranged symmetrically, such as in a square, rectangle, parallelogram, or isosceles trapezoid arrangement.

The various ideas and concepts presented in this application may be combined, in any combination, with other ideas and concepts presented in this application. For example, the discussion on a single opening having multiple light channels accompanying FIGS. 33-38 is applicable to the implementation of FIG. 43. The discussion on a single optical bundle having a light combiner connected to a light source and photodetector accompanying FIG. 39 is also applicable to the implementation of FIG. 43.

Such an arrangement may be suitable where the tissue, i.e., nerve, to be measured is large enough such that the source and detector structures can be placed over the tissue. For example, such an arrangement may be used in veterinary applications where the patient may be a large animal such as a horse, cow, gorilla, tiger, lion, elephant, rhinoceros, or bull.

Figure 44:
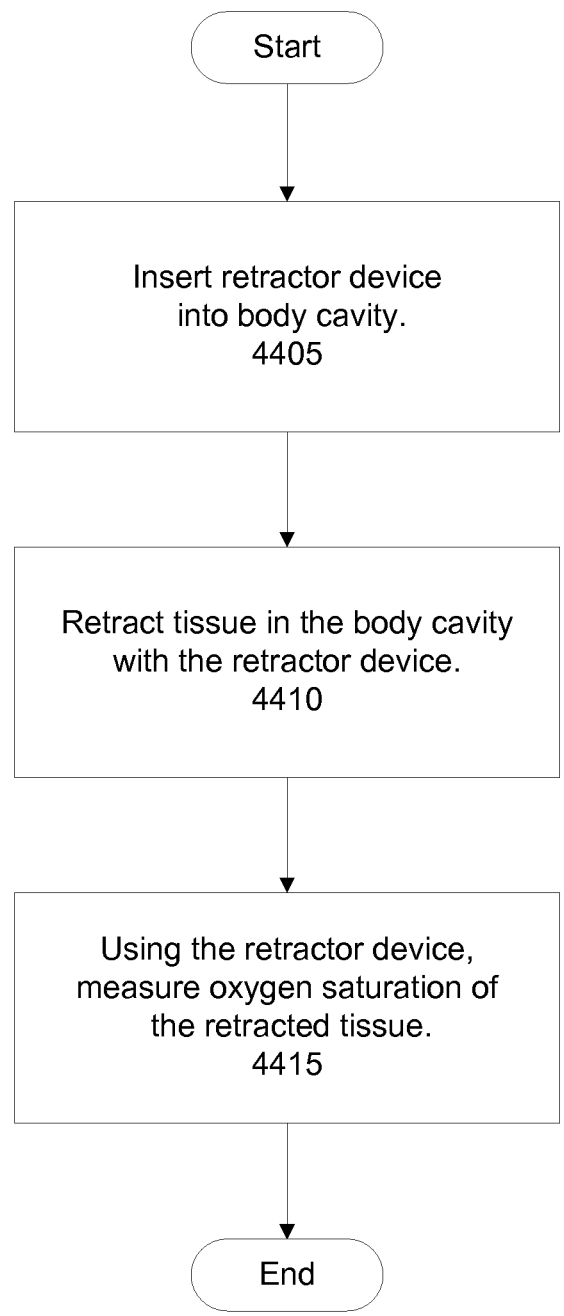
FIG. 44 shows a flow diagram representative of a user using a retractor.

FIG. 44 shows a flow diagram representative of a user using a retractor. In a step 4405, the user inserts a retractor device into a body cavity. For example, the body cavity may be an incision or wound. Typically, the body cavity will be in a human, but may be in any living organism such as animals, mammals, amphibians, reptiles, horses, cows, elephants, monkeys, dogs, cats, birds, fish, and pigs.

In a step 4410, the user retracts tissue in the body cavity with the retractor. Typically, the tissue is retracted using a pulling motion, but may also be retracted using a pushing motion. Generally, the tissue is a nerve, such as a nerve root. However, any type of tissue may be retracted (e.g., muscles and organs).

In a step 4415, the oxygen saturation of the retracted tissue is measured using the retractor. In a specific embodiment, the measurement is made using a tissue oximeter. However, the measurement may also be made using different techniques such as pulse oximetry.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
   a shaft, comprising a first bend, wherein from a distal end of the shaft to the first bend, the shaft extends in a first direction, and from the first bend to a proximal end of the shaft, the shaft extends in a second direction, which is different from the first direction;
   a handle, coupled to a proximal end of the shaft, extending in a second direction;
   a tip, coupled to a distal end of the shaft, comprising a retractor portion and an oximeter sensor on a bottom surface of the tip, wherein the retractor portion comprises a blade having a first edge and a second edge, opposite to the first edge, a first thickness between the first and second edges, the first edge has a first length that is greater than the first thickness, the first edge is closer to the bottom surface than the second edge, and the blade extends from the bottom surface in a third direction away from an axis that passes through the shaft;
   a first optical fiber;
   a second optical fiber, wherein the first optical fiber passes through a channel in the shaft and a distal end of the first optical fiber is coupled to a first sensor opening of the tip, and the second optical fiber passes through the channel in the shaft and a distal end of the second optical fiber is coupled to a second sensor opening of the tip,
   the first sensor opening is positioned on the bottom surface of the tip a first distance from the first edge, the second sensor opening is positioned on the bottom surface of the tip a second distance from the first edge, and the first distance is the same as the second distance; and
   a system unit comprising a display, processor, signal emitter circuit, signal detector circuit, and a receptacle to couple to proximal ends of the first and second optical fibers, wherein the signal emitter circuit sends a signal through the first optical fiber and the signal detector circuit receives the signal from the second optical fiber.

2. The device of claim 1 wherein the system unit comprises a power management circuit, a battery recharger circuit, and a rechargeable battery comprising lithium ion battery chemistry,
   when the power management circuit detects a low battery condition, the power management circuit causes a warning to show on the display,
   when the power management circuit detects a specified amount of time of inactivity has occurred, darkening the display, wherein the specified amount of time of inactivity is programmable by a user, and when the system unit detects that an oxygen saturation level measurement falls below a threshold value, displaying a warning message on the screen, wherein warning lights are positioned on a handle of the retractor, and the system unit causes the warning lights of the retractor to light.

3. The device of claim 1 wherein the first sensor opening and second sensor opening are separated by a distance from at least about 1.5 millimeters to about five millimeters.

4. The device of claim 1 wherein the console comprises a modem for transmitting oximetry data via a wireless communication network.

5. The device of claim 1 wherein the first length of the first edge of the blade of the retractor portion is less than a width of the shaft.

6. The device of claim 1 wherein the bottom surface of the tip comprises a textured surface comprising a plurality of protrusions.

7. The device of claim 1 wherein the tip comprises a first portion extending a first distance from the axis of the shaft in a first direction, a second portion extending a second distance from the axis a second direction that is opposite to the first direction, and the first edge of the retractor extends across the axis so there are first edge portions on opposite sides of the axis.

8. The device of claim 1 wherein to measure oxygen saturation of tissue touching the tip of device, the system unit
determines a first quantity corresponding to an intensity of light of a first wavelength transmitted from the first sensor opening of the tip through the tissue to the second sensor opening of the tip;
determines a second quantity corresponding to an intensity of light of a second wavelength transmitted from the first sensor opening of the tip through the tissue to the second sensor opening of the tip, wherein the second wavelength is different from the first wavelength; and
calculates an attenuation ratio of the first quantity to the second quantity, wherein the attenuation ratio is expressed by $$R(S, D) = \frac{U^{\lambda_1}(S, D)}{U^{\lambda_2}(S, D)},$$

where $U^{\lambda_i}(S,D)$ for i=1, 2, is the light intensity received by the first sensor when the second sensor is on at wavelength $\lambda_i$.

9. The device of claim 1 wherein the oximeter sensor comprises three or more holes in a first linear arrangement on a bottom side of the tip, a first line of the first linear arrangement is transverse to the axis of the shaft, and at least one of the three or more holes are on a first side of the axis while a remainder of the holes are on a second side of the axis, opposite to the first side.

10. The device of claim 1 wherein the oximeter sensor comprises four or more holes, where any two of the four or more holes are positioned in a second linear arrangement on the bottom surface of the tip, a second line of the second linear arrangement is not collinear with the first line, and at least one of the four or more holes are on a first side of the axis while a remainder of the holes are on a second side of the axis, opposite to the first side.

11. The device of claim 1 wherein the oximeter sensor comprises a first sensor emitter opening, a second sensor emitter opening, a first sensor detector opening, and a second sensor detector opening, and
the first sensor emitter opening on a first side of the axis while at least one of the second sensor emitter opening or the first sensor detector opening is on a second side of the axis, opposite to the first side.

12. The device of claim 1 wherein when force applied at the handle in a third direction, a component of the force in the third direction is applied to a tissue by the first edge of the retractor.

13. The device of claim 7 wherein a sum of the first distance and the second distance is less than a width of the shaft.

14. The device of claim 1 wherein the system unit determines tissue oxygenation by using an attenuation ratio expressed by $$R(S, D) = \frac{U^{\lambda_1}(S, D)}{U^{\lambda_2}(S, D)},$$

where $U^{80}{}_i(S,D)$ for i =1, 2, is the light intensity received by the first sensor when the second sensor is on at wavelength $\lambda_i$.

15. The device of claim 14 wherein the first and second sensors are arranged linearly, and oxygen saturation is expressed by $$StO_2(S_i, D_j) = kR(S_i, D_j) + b,$$

wherein k and b comprise calibration factors.

16. The device of claim 1 wherein the retractor portion comprises a retractor blade having an arc shape.

17. The device of claim 1 wherein the tip comprises a first portion extending a first distance from the axis in a first direction, a second portion extending a second distance from the axis a second direction that is opposite to the first direction, and a blade of the tip extends across the axis so there are blade portions on opposite sides of the axis.

18. The device of claim 1 wherein the channel of the shaft forms a portion of an internal passageway of the device through which the first and second optical fibers are entirely enclosed within from the openings at the tip to at least the proximal end of the shaft.

19. A device comprising:
a shaft;
a handle, coupled to a proximal end of the shaft; and
a tip, coupled to a distal end of the shaft, comprising a tissue oximeter sensor having a first opening and a second opening, wherein the first and second openings each have at least one light channel on a bottom surface of the tip, wherein the tissue oximeter sensor can make oxygen saturation measurements of tissue where there is no blood flow or pulse,
an axis passes through the shaft, and the tip comprises a first portion extending a first distance from the axis in a first direction, a second portion extending a second distance from the axis a second direction that is opposite to the first direction, and a retractor blade of the tip extends across the axis so there are blade portions on opposite sides of the axis, wherein the retractor blade comprises a first edge and a second edge, opposite to the first edge, a first thickness between the first and second edges, the first edge has a first length that is greater than the first thickness, the first edge is closer to the bottom surface than the second edge, and the blade extends from the bottom surface in a third direction away from an axis that passes through the shaft,
a sum of the first distance and the second distance is less than a width of the shaft, the first opening is positioned on the bottom surface of the tip a third distance from the first edge, the second opening is positioned on the bottom surface of the tip a fourth distance from the first edge, and the third distance is the same as the fourth distance, and
at least one optical fiber is coupled to the opening of the tip, and the at least one optical fiber is entirely enclosed within an internal channel of the device from the opening of the tip to at least the proximal end of the shaft.

20. The device of claim 19 wherein the first opening comprises a first optical fiber and a second optical fiber.

21. The device of claim 19 wherein the first opening comprises a concentric core fiber.

22. The device of claim 19 wherein the first opening comprises a split channel fiber.

23. The device of claim 19 wherein the handle comprises a shape adapted to be gripped by a human hand.

24. The device of claim 19 wherein the retractor blade comprises an arc shape, a first portion of the arc shape is on a first side of the axis, and a second portion of the arc shape is on a second side of the axis, opposite to the first side.

25. The device of claim 19 wherein a top side of the tip, opposite of the bottom side, comprises no openings, and
the retractor blade is transverse with respect to the bottom side of the tip.

26. The device of claim 19 wherein force applied at the handle comprises a component in the direction of an axis of the shaft to retract a tissue held against the retractor blade.

27. The device of claim 19 the retractor blade extends at an angle with respect to the bottom side of the tip, the first and second openings are positioned between the retractor blade and the shaft, and a line through the first and second openings is transverse to an axis of the internal channel of the tip through which the optical fiber passes.

28. A device comprising:
a tip comprising a retractor portion and an oximeter sensor formed on a bottom surface of the tip, wherein the retractor portion comprises a blade having a first edge that has a length greater than a thickness of the blade, and the blade extends from a tip of the first edge to the bottom surface, and from first edge to the bottom surface, the tip comprises a first turn in a first turn direction and the tip extends in a first direction;
a shaft, comprising a second turn in the first turn direction, wherein a distal end of the shaft is coupled to the tip, and from the distal end of the shaft to the second turn of the shaft, the shaft extends in a first direction, and from the second turn to a proximal end of the shaft, the shaft extends in a second direction, which is different from the first direction;
a handle, coupled to the proximal end of the shaft, wherein the handle extends from the proximal end of the shaft to a proximal end of the handle in the second direction,
wherein a first axis of the first turn is transverse to a second axis passing through the shaft from the distal end of the shaft to a second turn;
a first optical fiber; and
a second optical fiber, wherein the first optical fiber passes through a channel in the shaft and a distal end of the first optical fiber is coupled to a first sensor opening of the tip, and the second optical fiber passes through the channel in the shaft and a distal end of the second optical fiber is coupled to a second sensor opening of the tip,
the blade extends from the bottom surface in a third direction away from an axis that passes through the shaft, and
the first sensor opening is positioned on the bottom surface of the tip a first distance from the first edge, the second sensor opening is positioned on the bottom surface of the tip a second distance from the first edge, and the first distance is the same as the second distance.

29. The device of claim 28 wherein from the distal end of the shaft to the second turn of the shaft, the shaft comprises a straight length L1.

30. The device of claim 28 wherein from the second turn of the shaft to the proximal end of the shaft, the shaft comprises a straight length L2, and L1 is longer than L2.

31. The device of claim 28 wherein the bottom surface of the tip comprises the first and second opening and a textured surface comprising a plurality of nubs.

32. The device of claim 28 comprising:
a system unit comprising a display, processor, signal emitter circuit, signal detector circuit, and a receptacle to couple to proximal ends of the first and second optical fibers, wherein the signal emitter circuit sends a signal through the first optical fiber and the signal detector circuit receives the signal from the second optical fiber.

33. The device of claim 28 wherein the handle comprises a near-infrared light radiation source, coupled via the first optical fiber to the first sensor opening of the tip.

34. A device comprising:
a shaft, comprising a first internal channel extending from a proximal end to a distal end of the shaft;
a handle, coupled to a proximal end of the shaft, wherein the handle comprises an elongated member comprising:
a second internal channel extending from a first end and to a second end of the handle that is opposite the first end;
a first opening at the first end, coupled to the shaft; and
a second opening at the second end,
wherein the second internal channel is coupled to the first internal channel, and the second internal channel from the first end to the second end is linear;
a tip, coupled to the distal end of the shaft, comprising a third internal channel coupled to the first internal channel, a retractor blade and an oximeter sensor, wherein the third internal channel extends through the tip to at least two sensor openings of the tip, and an axis of the shaft passes through the retractor blade, and
the retractor blade comprises a first edge and a second edge, opposite to the first edge, a first thickness between the first and second edges, the first edge has a first length that is greater than the first thickness, the first edge is closer to a bottom surface of the tip than the second edge, and the blade extends from the bottom surface in a first direction away from the axis of the shaft;
a first optical fiber;
a second optical fiber, wherein the first optical fiber passes through the first, second, and third internal channels, and a distal end of the first optical fiber is coupled to a first sensor opening of the tip, and the second optical fiber passes through the first, second, and third internal channels and a distal end of the second optical fiber is coupled to a second sensor opening of the tip, and
the first sensor opening is positioned on the bottom surface of the tip a first distance from the first edge, the second sensor opening is positioned on the bottom surface of the tip a second distance from the first edge, and the first distance is the same as the second distance; and
a system unit comprising a display, processor, signal emitter circuit, signal detector circuit, and a receptacle to couple to proximal ends of the first and second optical fibers, wherein the signal emitter circuit sends a signal through the first optical fiber and the signal detector circuit receives the signal from the second optical fiber, and when the handle is moved in a second direction, the retractor blade of the tip moves in the second direction to cause a retraction of tissue, and when the handle is moved in a third direction, opposite the second direction, the retractor blade moves in the third direction to decrease a retraction distance.

35. The device of claim 34 wherein a length of the retractor blade is less than a width of the shaft.

36. The device of claim 34 wherein the bottom surface of the tip comprises the first and second opening and a textured surface comprising a plurality of protrusions.

37. The device of claim 34 wherein the tip comprises a first portion extending a first distance from the axis of the shaft in a fourth direction, a second portion extending a fifth distance from the axis a second direction that is opposite to the first direction, and the retractor blade extends across the axis so there are blade portions on opposite sides of the axis.

* * * * *